United States Patent [19]

Gerrone

[11] Patent Number: 5,320,608
[45] Date of Patent: Jun. 14, 1994

[54] COMBINED PNEUMO-NEEDLE AND TROCAR APPARATUS

[76] Inventor: Carmen J. Gerrone, 110 Dunkard Church Rd., Stockton, N.J. 08559

[21] Appl. No.: 42,488

[22] Filed: Apr. 2, 1993

Related U.S. Application Data

[63] Continuation-in-part of Ser. No. 10,769, Jan. 29, 1993.

[51] Int. Cl.$^5$ ............ A61M 5/00; A61M 5/178; A61M 25/00
[52] U.S. Cl. ............................ 604/117; 604/264; 604/164
[58] Field of Search ............ 604/51, 117, 164–170, 604/158, 264, 274

[56] References Cited

U.S. PATENT DOCUMENTS

| | | |
|---|---|---|
| 3,459,189 | 8/1969 | Alley et al. |
| 3,833,003 | 9/1974 | Taricco ............ 604/164 |
| 4,249,541 | 2/1981 | Pratt . |
| 4,535,773 | 8/1985 | Yoon . |
| 4,601,710 | 7/1986 | Moll . |
| 4,642,101 | 2/1987 | Krolikowski ............ 604/164 |
| 4,686,984 | 8/1987 | Bonnet . |
| 4,698,056 | 10/1987 | Cianella ............ 604/264 |
| 4,760,847 | 8/1988 | Vaillancourt . |
| 4,808,157 | 2/1989 | Coombs . |
| 4,960,412 | 10/1990 | Fink ............ 604/167 |
| 4,986,814 | 1/1991 | Barney et al. |
| 4,994,042 | 2/1991 | Vadher . |
| 5,057,082 | 10/1991 | Burchette, Jr. . |
| 5,059,183 | 10/1991 | Semrad . |
| 5,066,288 | 11/1991 | Deniega et al. |
| 5,122,122 | 6/1992 | Allgood ............ 604/167 |
| 5,135,525 | 8/1992 | Biacoping et al. |
| 5,147,316 | 9/1992 | Castillenti ............ 604/174 |
| 5,183,465 | 2/1993 | Xanthakos ............ 604/117 |
| 5,207,649 | 5/1993 | Aruny ............ 604/167 |
| 5,217,441 | 6/1993 | Shichman ............ 604/164 |
| 5,226,426 | 7/1993 | Yoon ............ 604/165 |

FOREIGN PATENT DOCUMENTS 1445713 12/1988 U.S.S.R. .

Primary Examiner—C. Fred Rosenbaum
Assistant Examiner—Frank Wilkens
Attorney, Agent, or Firm—Mathews, Woodbridge & Collins

[57] ABSTRACT

A trocar houses a pneumo-needle, the cutting tip of which emerges eccentrically or concentrically from the tip of the trocar. An obturator, in turn, is housed within said pneumo-needle and is controlled at the distal end of the pneumo-needle by a spring release button. A cannula and reducer housing surround the trocar and are selectively attachable to a needle retainer which controls the penetration of the obturator, pneumo-needle, trocar and cannula into the abdominal cavity. A latch mounted on the rear of the needle retainer permits the pneumo-needle to selectively slide with respect to the needle retainer. Graduations on the needle permit the surgeon to set the depth of penetration of the pneumo-needle. The latch controls the depth of penetration of the pneumo-needle beyond the front face of the needle retainer. The pneumo-needle, in turn, acts as a pilot and controls the depth of penetration of the trocar and cannula. A cannula stop mounted on the needle retainer sets the depth of penetration of the trocar and cannula and permits the cannula to selectively slide with respect to the needle retainer. The apparatus allows the surgeon to employ the full length of the pneumo-needle as a pilot without having to partially withdraw the pneumo-needle prior to inserting the trocar and cannula.

23 Claims, 20 Drawing Sheets

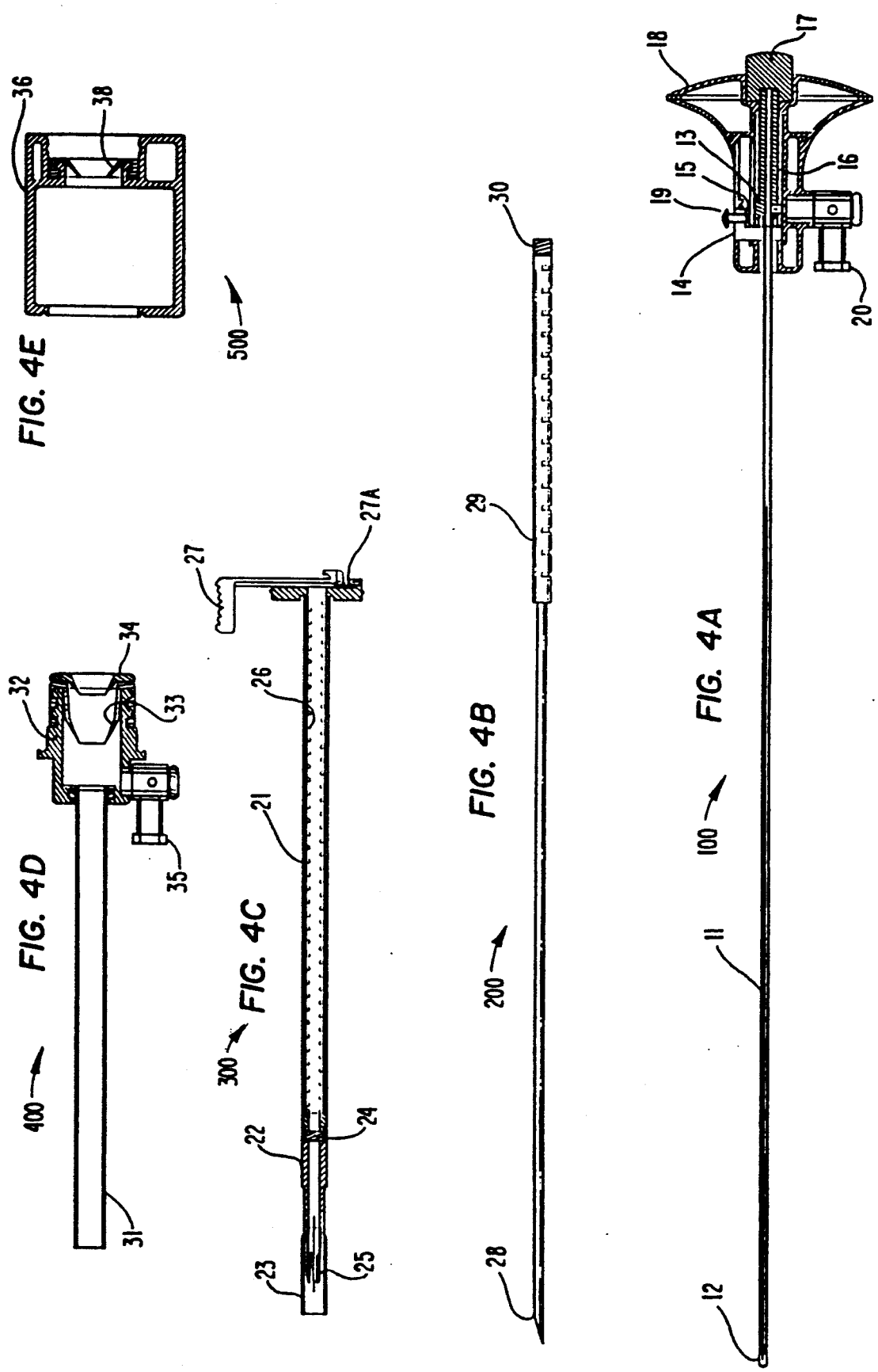

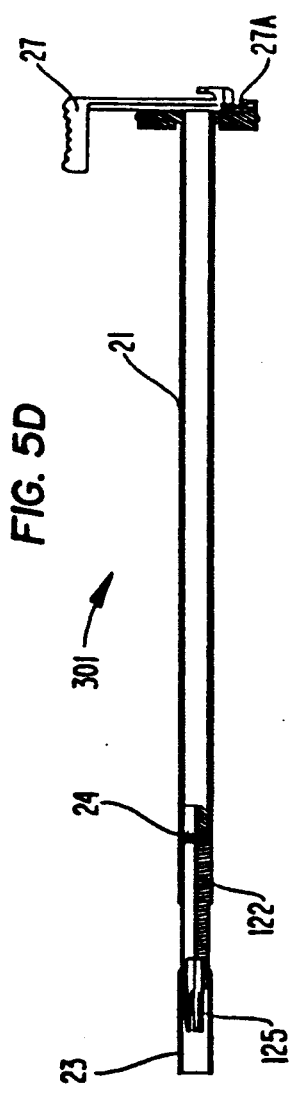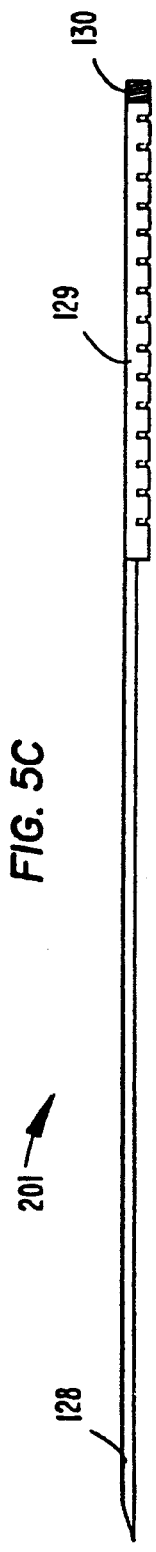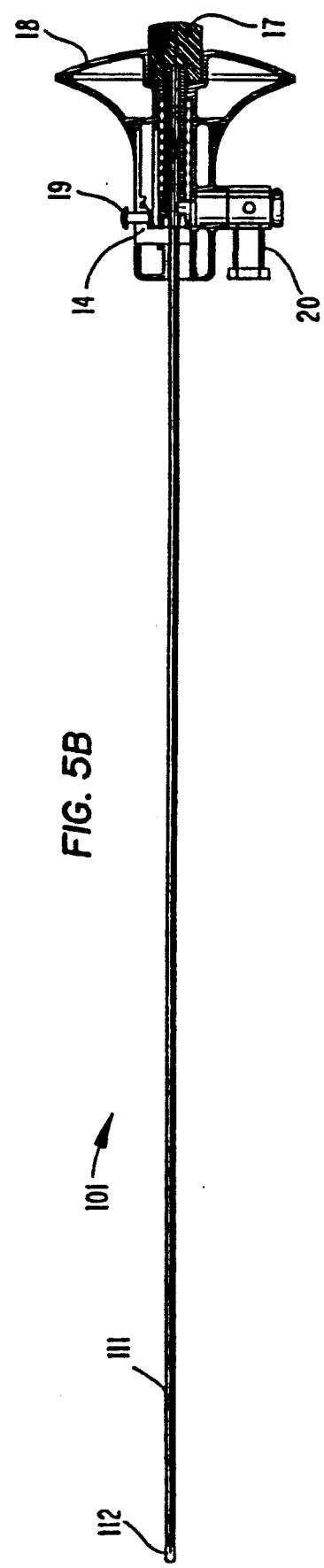

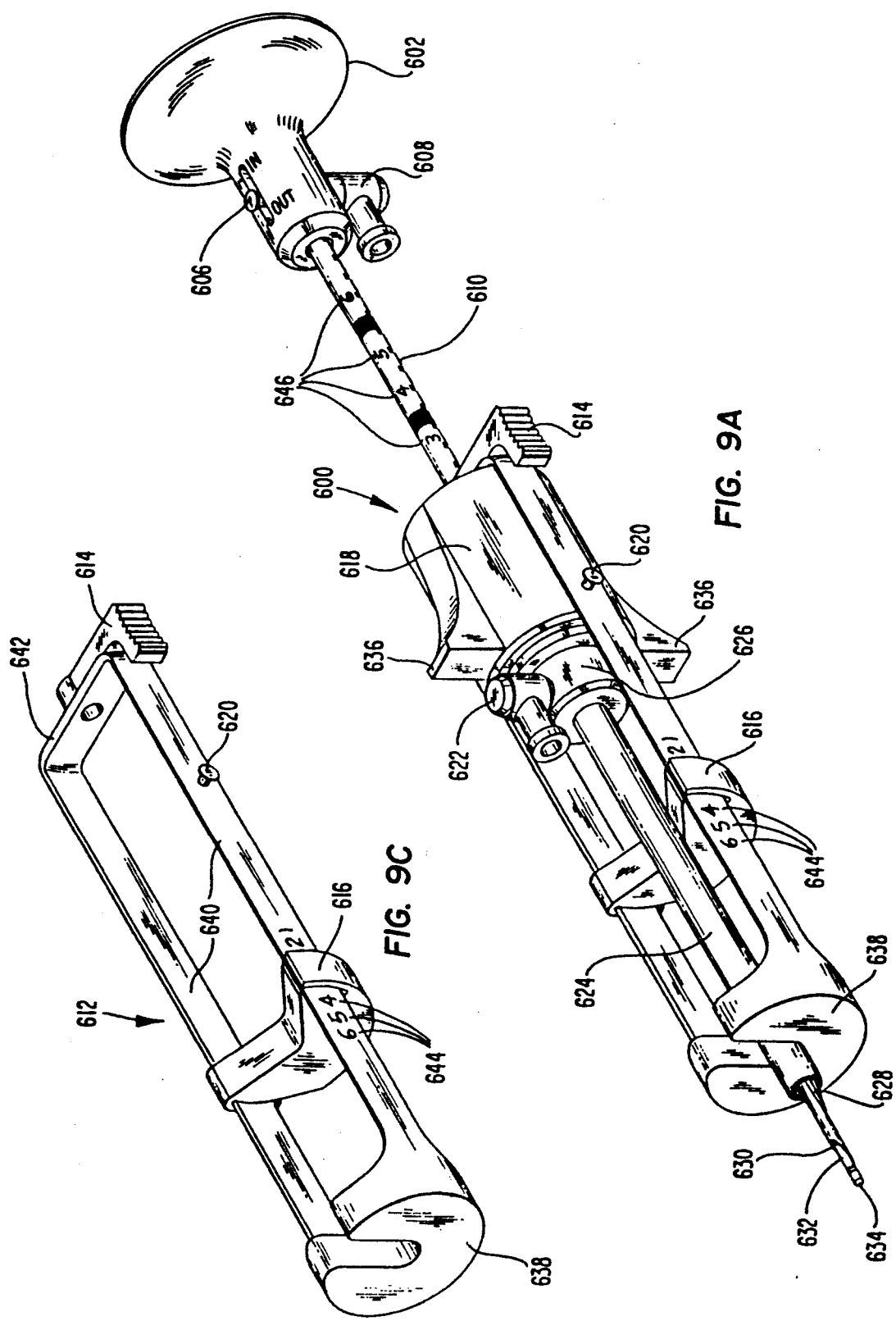

COMBINED PNEUMO-NEEDLE AND TROCAR APPARATUS

CROSS-REFERENCE TO RELATED APPLICATION

This application is a continuation-in-part of my copending U.S. patent application Ser. No. 08/010,769 filed on Jan. 29, 1993, allowed Nov. 16, 1993 the entire contents and substance of which are hereby incorporated by reference into this application.

BACKGROUND OF THE INVENTION

1. Field of the Invention

This invention relates to medical instruments and, in particular, to a trocar that houses a pneumo-needle for making the pilot entry wound.

2. Description of Related Art

Trocars are sharp pointed surgical instruments used to puncture a body cavity. This is frequently done so that fluids can be drained using a cannula inserted into the opening. Trocars are also used during endoscopic and laparoscopic diagnostic and therapeutic procedures. A conventional endoscopic procedure follows three steps. The first step is the insertion of a Veress cannula into the abdominal cavity through a small incision in the abdominal wall. The Veress cannula includes a hollow pneumo or Veress needle having a sharp point. When the cavity is entered, a spring-loaded obturator inside the lumen of the needle pops out to extend a short distance beyond the needle's sharp point. This protects against an inadvertent laceration of intra-abdominal structures. Because the obturator is spring-loaded, it is not able to protrude beyond the needle's point until the abdominal cavity is entered. Next, the abdominal cavity is inflated with a gas through a small lumen in the obturator of the Veress cannula. After inflation, the Veress cannula is removed. Finally, a standard trocar housed within the lumen of a trocar tube is thrust into the inflated abdomen to increase the size of the opening. Standard trocars are shaped like a large metal peg with a sharpened point, having a diameter varying from 3–12 mm. The trocar is then removed and an endoscopic instrument is inserted into the abdominal cavity through the trocar tube.

A major problem with standard trocars is that the sharpened tip of the trocar, after being thrust through the abdominal wall, can inadvertently puncture or lacerate intra-abdominal tissue. Also, standard conventional trocars are generally not disposable and after reuse, the tips become dull, requiring frequent sharpening, otherwise the force to enter the abdomen gets unacceptably high.

U.S. Pat. Nos. 4,601,710 and 4,535,773 describe embodiments of a disposable trocar which include a spring-bodied tubular protective shield. One embodiment describes a trocar whose piercing tip is formed of three blades. The shield of this trocar is a tubular body having a frustoconical end that is slotted to receive the blades. In a second embodiment, which was considered to be an improvement over the first, the piercing tip is pyramidal and is formed by three bevels in the end of an otherwise cylindrical body. The second embodiment also has a shield locking mechanism. Both embodiments also have sealing valves within the cannula tube, to prevent gas leaking from the abdominal cavity during operative procedures. While these embodiments are an improvement over standard trocars, the cutting action and force required to thrust the trocar into the abdomen is still large due to the configuration of the cutting tip and the force required to compress the shield. This creates a plunging effect which results in a high probability of inadvertently striking and damaging abdominal tissues.

In addition to the above, current valve designs within the cannula tube do not optimally restrict gas leakage, and because of their configuration and action, they interfere with endoscopic instruments which pass through into the abdominal cavity. Further, the initial step of inserting the Veress cannula creates an additional hole. There is, therefore, a significant need: to improve the performance of the piercing tip to reduce the force of insertion of the trocar; to eliminate one step of the current procedure; to add levels of safety by controlling the depth of penetration of thrust, eliminating the plunging effect; and to improve the cannula seal to minimize gas leakage and reduce interference with endoscopic instruments passing through into the abdominal cavity.

A combined laparoscopic trocar and pneumo-needle is described in Soviet Patent SU 1445-713-A issued Dec. 23, 1988. That laparoscope trocar includes a pneumo-peritoneum needle with an introduction depth limiter and an underspring mandrel having a blunt working end. A socket on the working end includes a side aperture and a longitudinal groove in its inner surface which joins with the side aperture at a connection. In other words, the pneumo-needle is housed in a channel in the trocar. The Soviet device also includes an obturator safety tip and a depth control mechanism. The Soviet device, however, appears to have the drawback that it is relatively inflexible and difficult to manipulate. The intended use, function and design of the structure suggests that during the insertion step, after pneumo-peritoneum is created, the surgeon must continue to thrust the instrument into the abdominal cavity with the needle in the extended position. This presents a high risk of damage to internal organs because the pneumo-needle consumes the intended safety space created by the pneumo-peritoneum between abdominal wall and the organs. Therefore, the structure of the Soviet device appears to increase the risk of accidental puncture of internal organs.

Other patents describe combined pneumo-needles and trocars. See, for example, U.S. Pat. No. 4,535,773 which discloses a trocar having a needle which passes through the side of the tip. Other patents describe needles or guidewires which emerge from near the tip of a trocar-like puncture peg. Note specifically: U.S. Pat. Nos. 4,808,157; 5,135,525; and, 3,459,189.

Attempts have been made in the prior art to avoid making more puncture holes in the patient than are absolutely necessary. This concept is suggested, for example, in U.S. Pat. No. 4,986,814 entitled ONE-PUNCH CATHETER.

U.S. Pat. No. 4,994,042 entitled COMBINED CATHETER AND NEEDLE is of possible relevance in that it describes the combination of diverse puncture mechanisms.

U.S. Pat. No. 4,686,984 entitled CATHETER FOR WIDENING A PUNCTURE HOLE describes a device for widening puncture channels through the use of progressively bigger enlarging elements.

The following patents are cited with regard to their general teaching in the area of combined pneumo-needle and trocar devices: U.S. Pat. Nos. 4,249,541; 5,059,183 and 5,066,288.

The use of graduated scales in the context of a specific puncture mechanism is described in U.S. Pat. No. 4,760,847 and is discussed, to a limited extent, in Soviet Patent SU 1445-713-A, previously described.

There appears to be very little relevant art with regard to the use of stamped tips for trocar-like instruments. Of possible relevance, however, might be U.S. Pat. No. 5,057,082 entitled TROCAR ASSEMBLY which generally discusses the structure of a particular trocar tip but otherwise does not appear to be relevant to the concept of using stamped materials therefore.

The prior art taken as a whole does not appear to teach or suggest combining a pneumo-needle, trocar and sleeve into a single apparatus having the benefits of the present invention. Among the many benefits of the present invention are the elimination of the plunging effect by limiting penetration into the body cavity and the simultaneous reduction of force necessary to pierce the abdominal wall through the use of an eccentric located pilot needle. The one cycle locking feature of the obturator adds significant safety to the surgical procedure. Several other features of the invention are significant improvements over the prior art. The advantages of the combined eccentrically housed pneumo-needle/trocar invention are the following: a reduction in the number of steps with respect to prior art procedures; one fewer hole required to be made in the abdominal cavity; a piloted piercing tip with lower force required to thrust the trocar through the abdominal wall; a pneumo-needle obturator locking mechanism which provides visual, audible and tactile feedback to indicate when the abdominal cavity has been penetrated; a color-coded graduated pneumo-needle, which is setable in order to measure depth, coinciding with the patient's abdominal wall thickness, to which the pneumo-needle is to be penetrated into the abdominal cavity, thereby eliminating unnecessary plunging and the resultant possible tissue damage; a sealing means within the trocar tube which offers less interference than prior art devices to endoscopic instruments as they are manipulated during operative procedures and wherein the seals offer greater restriction with respect to gas leakage during procedures as the endoscopic instruments are passed through the device or after the trocar has been withdrawn; providing the availability of additional 1.5 mm and 3.0 mm access lumens within the same instrument; and, in general, a more suitably ergonometrically configured device. Finally, the prior art does not appear to teach or suggest the combining of a pneumo-needle with a trocar, cannula and sleeve into a single instrument wherein substantially all of the extended length of the pneumo-needle acts as a true pilot for the trocar, cannula and sleeve so as to minimize the risk of accidental puncture of internal organs.

SUMMARY OF THE INVENTION

Briefly described, the invention comprises a combined pneumo-needle and trocar apparatus in either of two embodiments in which the pneumo-needle is either concentrically or eccentrically located within the trocar. Another aspect of the invention is the use of a spring-loaded obturator having a resetable one-cycle locking mechanism. A color graduated, sharp needle, held in place by a latch means that permits separation from the obturator, allows 1.5 mm access through the needle lumen into the abdominal cavity. The obturator spring action provides visual, audible and tactile feedback with respect to its position during penetration. The latch means is engagable with depth control graduations on the needle barrel. The depth control graduations coincide with color coded measurements etched directly on the pneumo-needle that relate to patient wall thickness and can be preset to the desired depth of insertion into the abdominal cavity. The trocar also includes a sealing means within its lumen, to allow insertion of operative endoscopic instruments through a 3.0 mm access port without significant inflation gas leakage. The trocar includes a piercing tip configured with three sharp edges and a 3.0 mm lumen through which the pneumo-needle passes, wherein the needle acts as a pilot for the piercing tip when insertion is made through the abdominal wall.

The diameter of the pneumo-needle/trocar assembly within a cannula varies from 5–12 mm. A seal means in the cannula tube restricts leakage of inflation gases when the trocar is removed or when endoscopic instruments are inserted through the tube into the abdominal cavity. A stabilizer associated with the pneumo-needle/trocar/cannula/reducer assembly includes graduations for setting the controlled depth of penetration of the cannula into the patient's abdominal cavity. Once penetration is achieved, the interaction of the stabilizer and an abdominal lock provide for greater stabilization of the cannula above the abdomen and for a more secure engagement which helps to prevent the inadvertent withdrawal of the cannula from the patient.

Another alternative embodiment of the present invention contemplates the replacement of the existing trocar portion of a prior art reusable trocar with the pneumo-needle/trocar assembly of the present invention. This, when employed with a standard trocar cannula, improves the safety of a standard, prior art reusable trocar.

The preferred embodiment of the invention comprises a combined pneumo-needle and trocar apparatus in which the pneumo-needle is concentrically or eccentrically located within the lumen of the trocar. To this extent it achieves many of the benefits associated with the embodiments previously described. It differs, however, from the other embodiments in that the pneumo-needle and trocar are supported by and engaged with a needle retainer. The needle retainer acts as a needle penetration depth limiter during the first step of the insertion process by locking the pneumo-needle in place with respect to the retainer at a desired depth. After the pneumo-needle has been inserted to the precise depth, the trocar and cannula are then passed down substantially the entire length of the shaft of the pneumo-needle. In this sense, the pneumo-needle acts as a true pilot and controls the exact depth of trocar penetration because the trocar and cannula must follow exactly the same path as the pneumo-needle. This also forces the trocar and cannula to come to a stop at a precise location. This eliminates risk of injury to the tissues in the abdominal cavity during the trocar penetration step. It also provides the surgeon with an intra-operative selection of procedures to create pneumo-peritoneum. The surgeon has two choices, namely, to create peritoneum after the needle insertion step prior to full trocar insertion or after full trocar insertion into the abdominal cavity. These and other features of the invention will be more fully understood by reference to the following drawings.

BRIEF DESCRIPTION OF THE DRAWINGS

FIG. 4A is a cross-sectional view of the obturator and knob subassembly of the preferred concentric embodiment illustrated in FIGS. 1 and 2B.

FIG. 4B illustrates the pneumo-needle subassembly of the preferred concentric embodiment illustrated in FIGS. 1 and 2B.

FIG. 4C is a cross-sectional view of the trocar and latch subassembly of the preferred concentric embodiment illustrated in FIGS. 1 and 2B.

FIG. 4D is a cross-sectional view of the cannula, cannula housing and duckbill valve subassembly of the preferred concentric embodiment illustrated in FIGS. 1 and 2B.

FIG. 4E is a cross-sectional view of the reducer housing and reducer seal subassembly of the preferred concentric embodiment of the invention illustrated in FIGS. 1 and 2B.

FIG. 5B is a cross-sectional view of the obturator and knob subassembly of the alternative eccentric embodiment illustrated in FIG. 2A and 5A.

FIG. 5C illustrates the pneumo-needle subassembly of the alternative eccentric embodiment illustrated in FIGS. 2A and 5A.

FIG. 5D is a cross-sectional view of the trocar and latch subassembly according to the alternative eccentric embodiment illustrated in FIGS. 2A and 5A.

FIG. 9A is a front perspective view of the preferred embodiment of a combined, concentric pneumo-needle and trocar apparatus engaged with a needle retainer.

FIG. 9C is a front perspective view of the needle retainer sub-assembly according to the preferred embodiment of the invention illustrated in FIG. 9A.

DETAILED DESCRIPTION OF THE INVENTION

Figure 1:
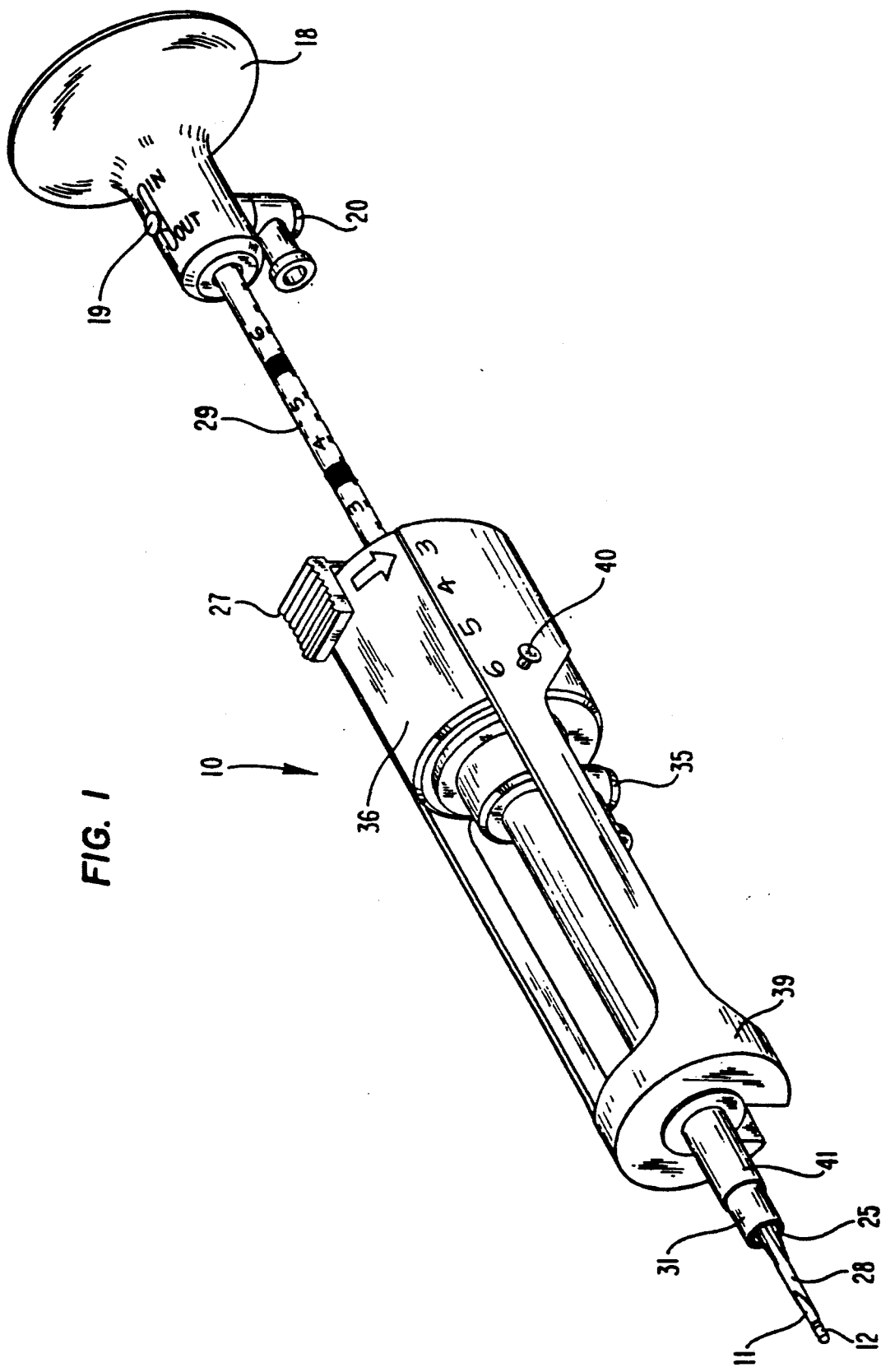
FIG. 1 is a front perspective view of a combined, concentric pneumo-needle and trocar apparatus according to the preferred embodiment of the invention.
Figure 2A:
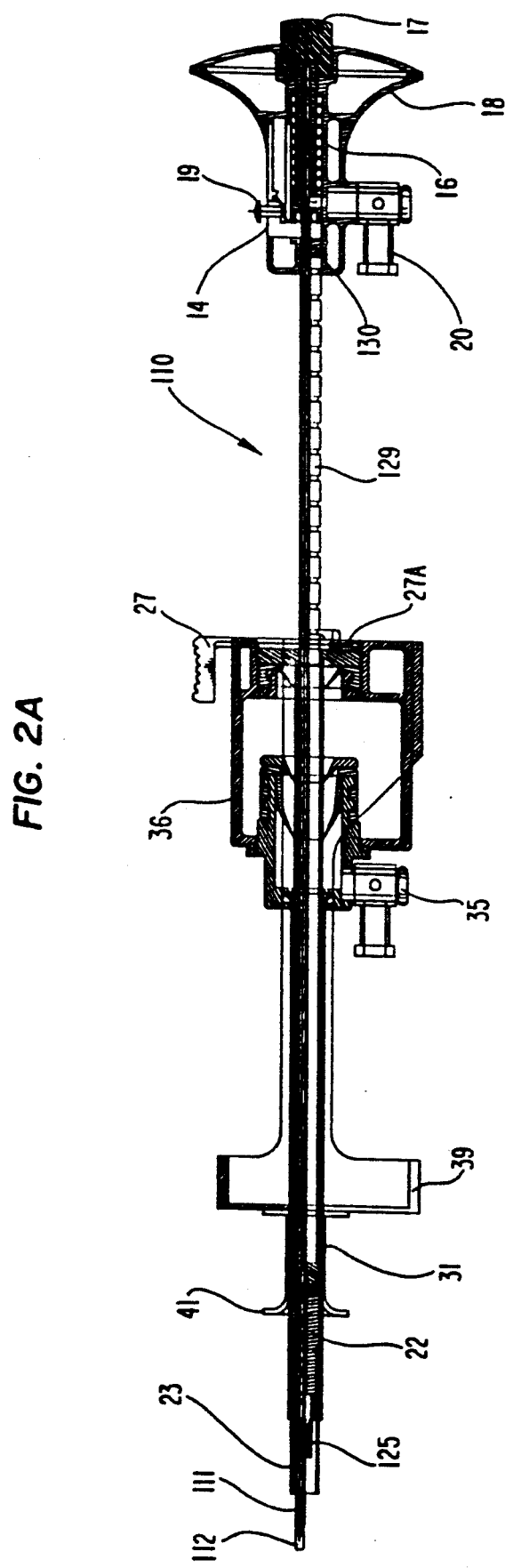
FIG. 2A is a vertical, cross-sectional illustration of an alternative embodiment of the invention in which the pneumo-needle is located eccentrically with respect to the central axis of the trocar.
Figure 2B:
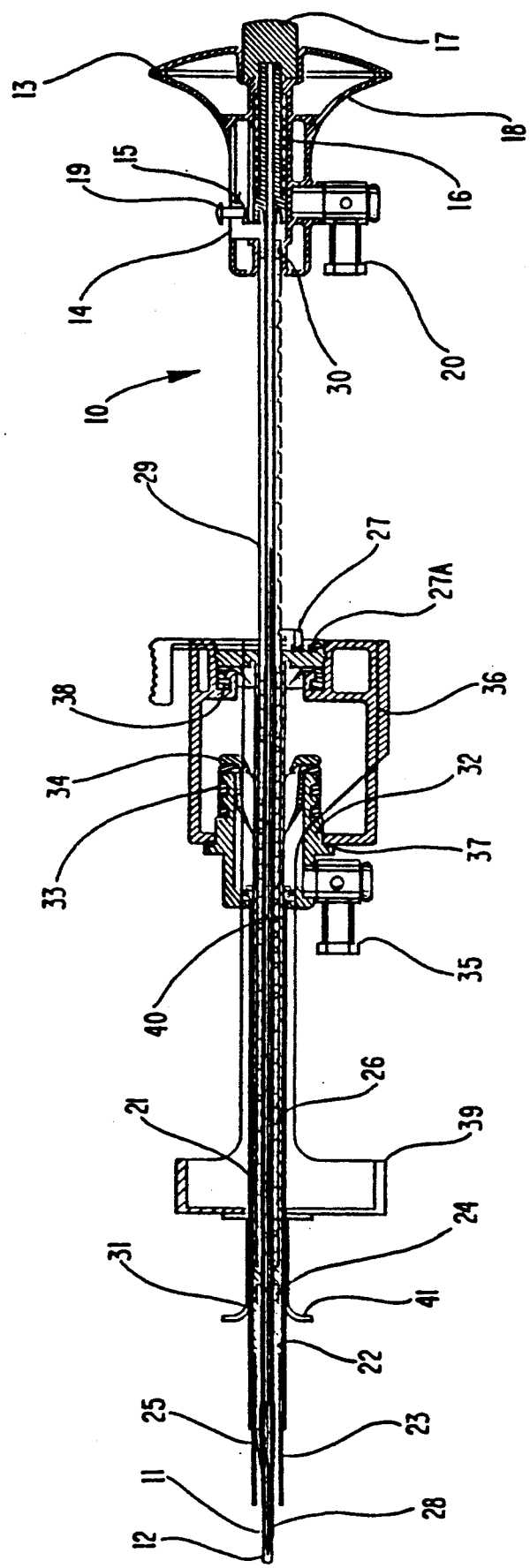
FIG. 2B is a vertical, cross-sectional illustration of the preferred concentric embodiment of the invention illustrated in FIG. 1.

During the course of this description, like numbers will be used to identify like elements according to the different Figures that illustrate the invention.

The invention primarily comprises a basic concentric embodiment 10 and an alternative eccentric embodiment 110. A complete description of the basic concentric embodiment 10 and the alternative eccentric embodiment 110 and related FIGS. 1-8B can be found in my copending U.S. patent application Ser. No. 08/010,769 filed Jan. 29, 1993, the entire contents of which are incorporated herein by reference. According to the preferred concentric embodiment 10, the pneumo-needle 28 is concentric with the trocar 21, that is to say they share a common long axis. The preferred concentric embodiment 10 is illustrated in FIGS. 1, 2B, 3, 4A, 4B, 4C, 4D, 4E, 6A, 6B, 6C, 6D, 7A, 7B, 7C, 7D, 8A and 8B. While the stamped trocar tip 70 illustrated in FIGS. 8A and 8B can be employed with the preferred concentric embodiment of the invention 10, it will be appreciated by those of ordinary skill in the art that other trocar tips may be used as well. The alternative eccentric embodiment of the invention 110 is illustrated in FIGS. 2A, 5A, 5B, 5C, 5D, 8C and 8D. According to the alternative eccentric embodiment 110, the pneumo-needle 128 is offset within the trocar 21. In other words, the long axis of the pneumo-needle 128 is offset by a distance "D" from the long axis of the trocar 21. Another alternative embodiment of the invention calls for the use of a depth setting adjuster screw 42 as illustrated in FIG. 7D. The following discussion of the preferred concentric embodiment 10 refers to FIGS. 1, 2B, 3, 4A, 4B, 4C, 4D, and 4E.

The preferred concentric embodiment 10 of the present invention is illustrated in a perspective view in FIG. 1. As seen from the exterior, the preferred embodiment 10 includes an obturator knob 18, an obturator housing cap 17, an obturator activating button 19, an obturator stop cock 20, a needle graduator 29, a trocar latch 27, a reducer housing 36, a second stop cock 35, a stabilizer 39, stabilizer lock 41, cannula 31, the trocar cutting tip 25, the cutting tip 28 of the pneumo-needle, the obturator 11 and the obturator tip 12.

The obturator subassembly 100, seen in FIG. 4A, includes obturator knob 18 that comprises two halves that, when snapped together, have forward finger positions and a rounded rear wall that fits comfortably in the hand of the surgeon. A rear exit port allows the passage of a cap 17 that extends beyond the rear wall of the knob 18 and connects to the spring-loaded obturator 11 that exits through a forward port, such that the inward and outward movement of the obturator 11 can be observed and tactilely felt via movement of the cap 17. An additional visual indication of the movement of obturator 11 is obtained by the activation of button 19 attached to housing 14 which is connected to and slides with the obturator 11. These two visual and tactile safety features indicate to the surgeon that the abdominal cavity 84 (see FIG. 7A–7B) has been entered. The surgeon then knows that the thrusting of the instrument into the abdominal cavity can cease. At that point, the obturator 11 has returned to its extended position and the sharp point of the needle 28 is not exposed, thereby preventing the inadvertent laceration of intra-abdominal structures.

A rubber obturator tip 12 located at the remote, or distal end of the obturator tube 11 from the obturator knob 18, provides a soft rounded surface that will not inadvertently penetrate the intra-abdominal organs. The knob assembly 18 located at the proximal end of the obturator tube 11 includes slider 13, housing 14, spring lock 15, spring 16 and actuating or release button 19. Also attached to actuator knob 18 is a stop cock 20 that is normally closed and in the down position. Stop cock 20 is opened by rotating it to the up position. The obturator tip 12 is biased forward by spring 16 and locked in position by obturator lock 15 which is controlled by knob 18. The obturator release button 19 releases lock 15 and permits the obturator tube 11 and tip 12 to slide rearwardly when force is placed on the tip 12. When force is removed, the obturator tip 12 springs forward and locks in position, requiring activation of the release button 19 to permit rearward motion again. Accordingly, the obturator tip 12 will not slide back exposing the sharp cutting needle 28 after the needle has penetrated the abdominal wall should contact be made with intra-abdominal structures. An access path through the stop cock 20, when rotated upwardly, knob 18 and slider 13, allows gas to pass to and through the obturator tube 11 to the distal end where a hole perpendicular to the obturator lumen allows gas to pass to inflate the abdomen. Obturator housing cap 17 is threadably engaged with slider 13. When cap 17 is unscrewed from slider 13, it exposes the obturator lumen, thereby permitting saline solution to be passed through in order to test and ensure complete abdominal entry.

Figure 7A:
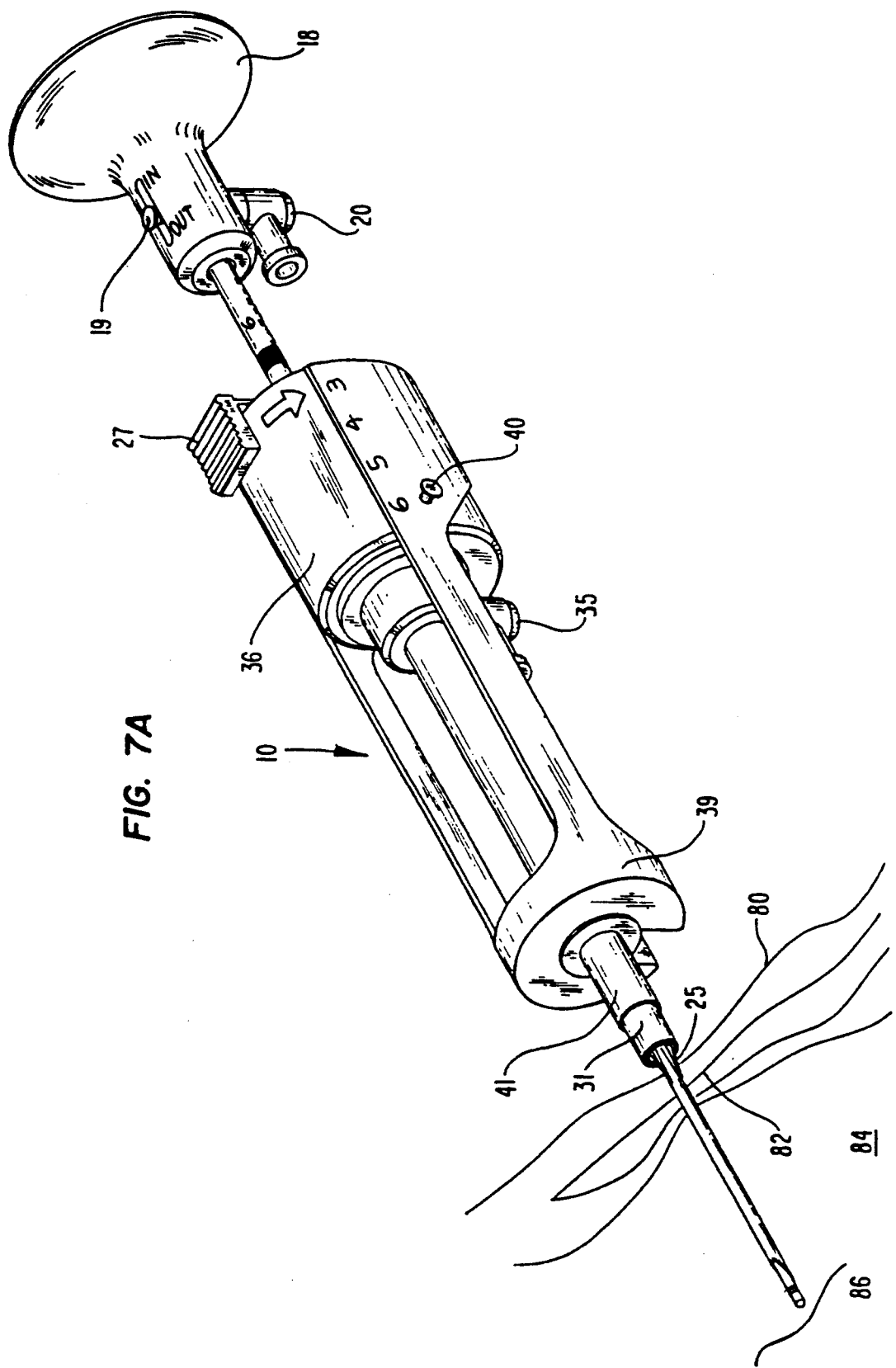
FIG. 7A illustrates an initial step in the use of the combined pneumo-needle/trocar invention according to the preferred concentric embodiment in which the pneumo-needle has just pierced the abdominal wall of the patient and the obturator tip is about to limit the depth of penetration of the pneumo-needle.
Figure 7B:
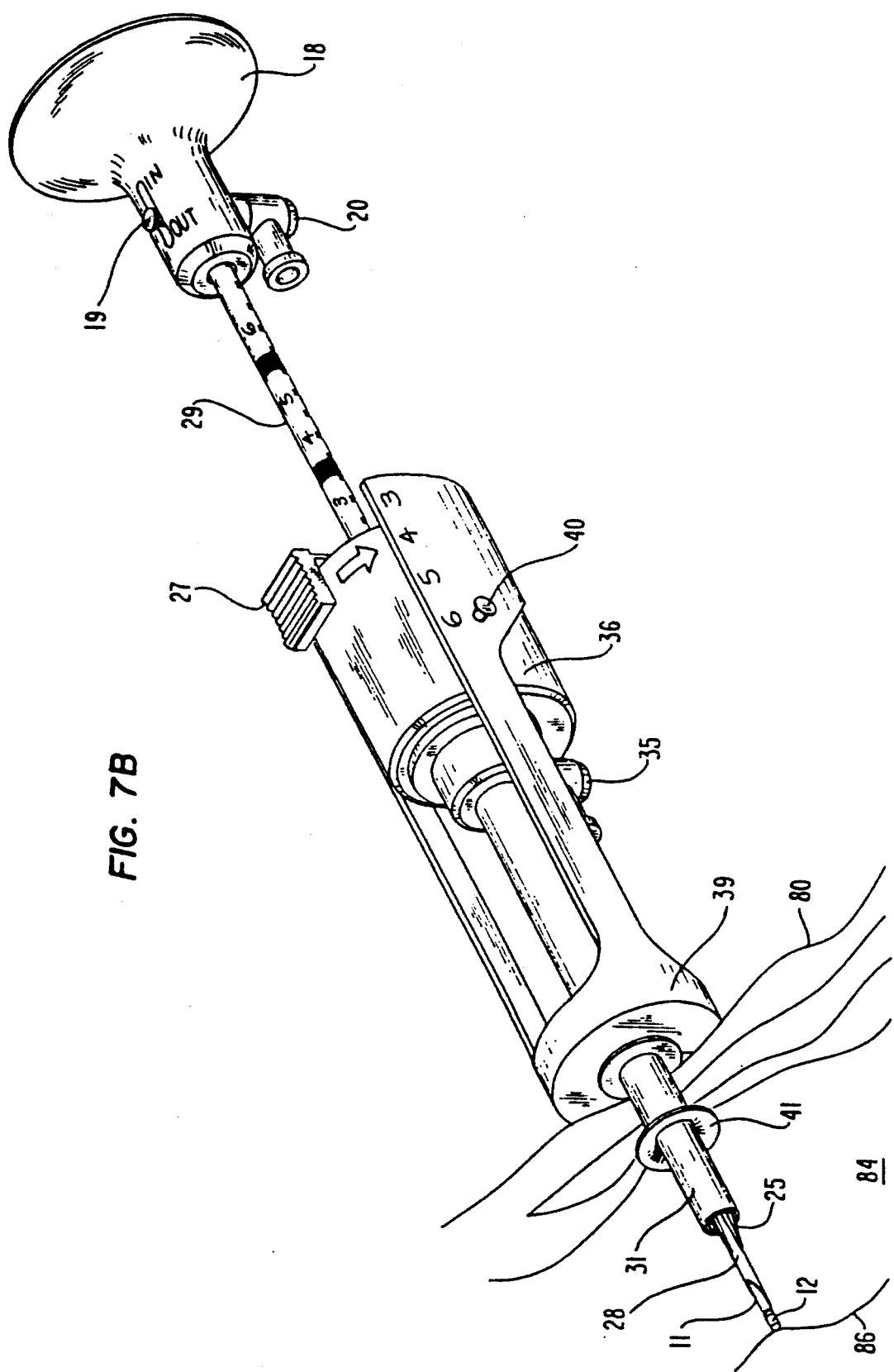
FIG. 7B illustrates a subsequent step in the use of the preferred concentric embodiment of the invention, wherein the trocar has been advanced down the pneumo-needle shaft and into the abdominal cavity up to a preset depth controlled by a depth setting mechanism.
Figure 7C:
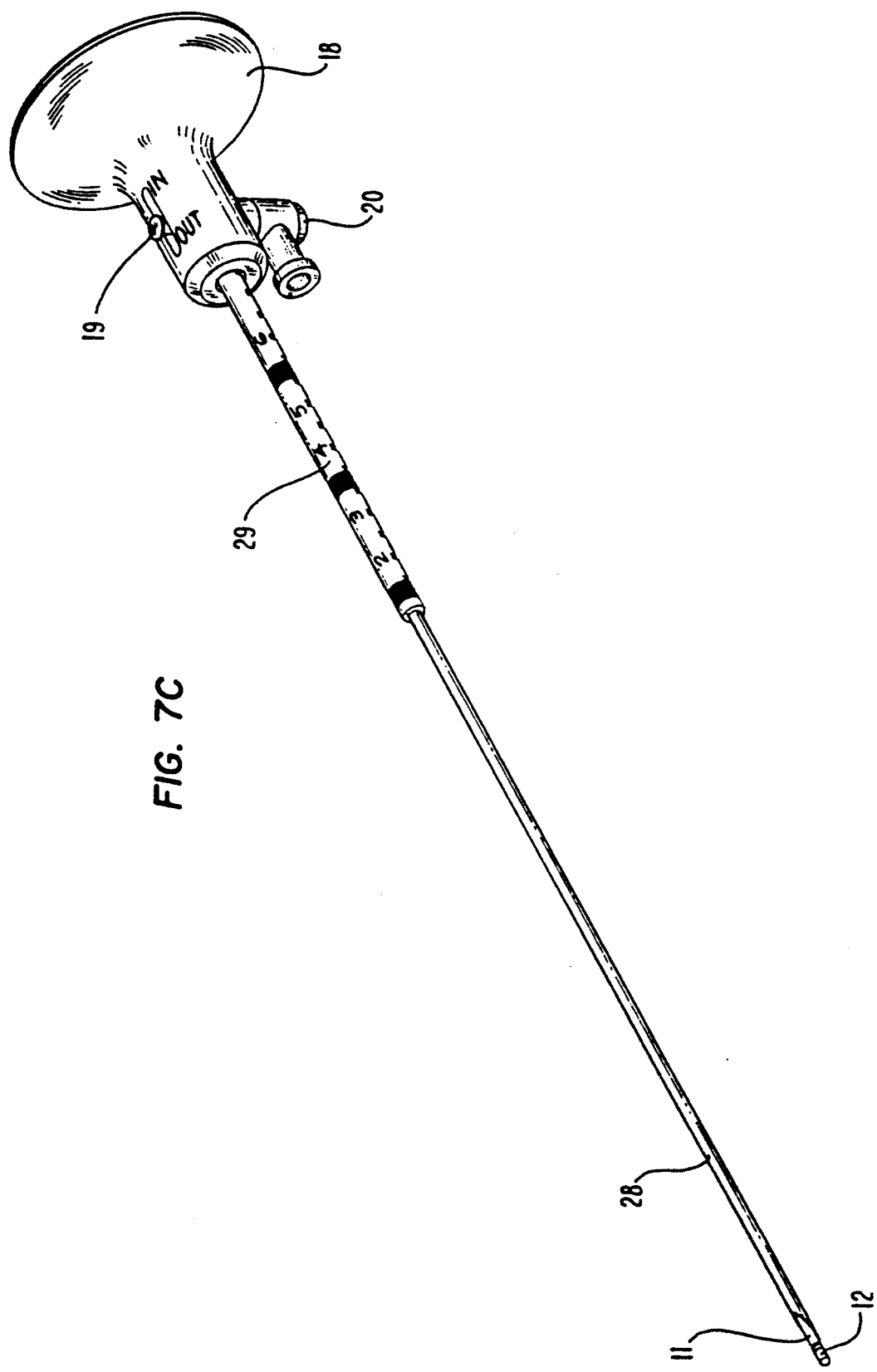
FIG. 7C illustrates the combination of the pneumo-needle and obturator knob and tip subassembly such as employed in the procedures illustrated in FIGS. 7A and 7B.
Figure 8A:
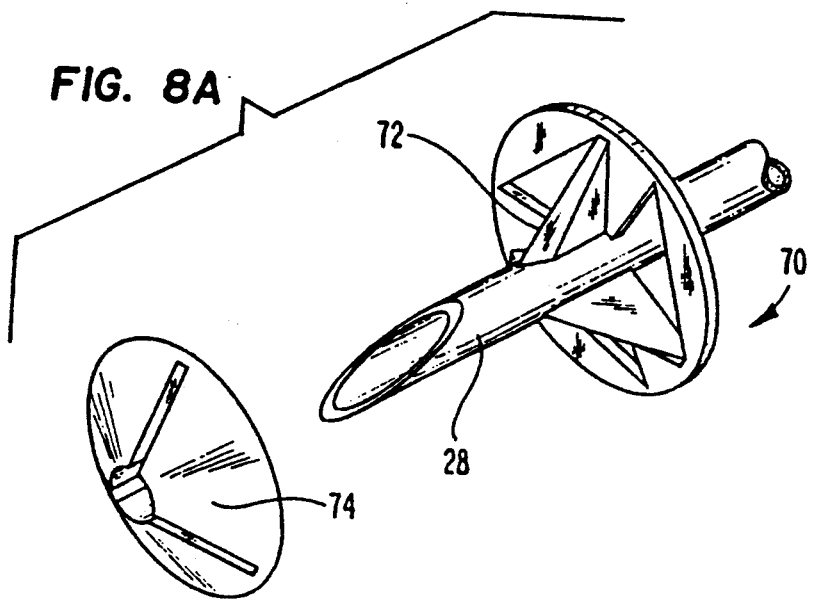
FIG. 8A is an exploded, perspective view of a concentric pneumo-needle and stamped trocar tip combination including a protective cap.
Figure 8B:
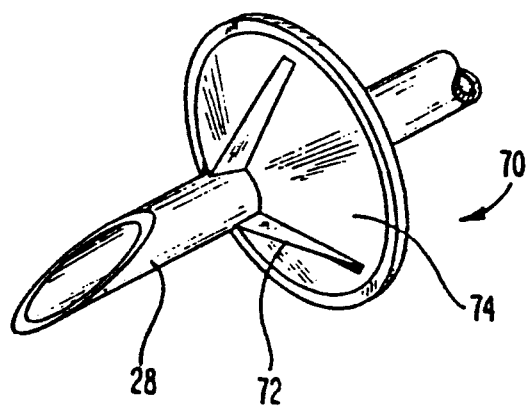
FIG. 8B is a perspective view of an assembled concentric pneumo-needle and stamped trocar tip combination including the protective cap in position over the stamped tip.
Figure 8C:
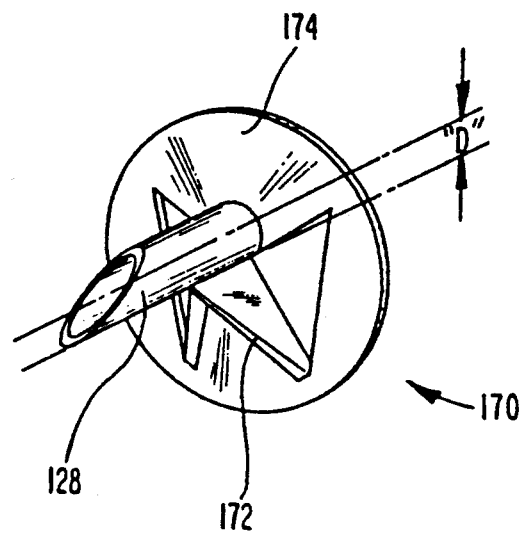
FIG. 8C is a perspective view of an eccentrically located pneumo-needle and stamped trocar tip with the pneumo-needle offset from the central axis of the stamped tip and the associated trocar by an offset distance "D."
Figure 8D:
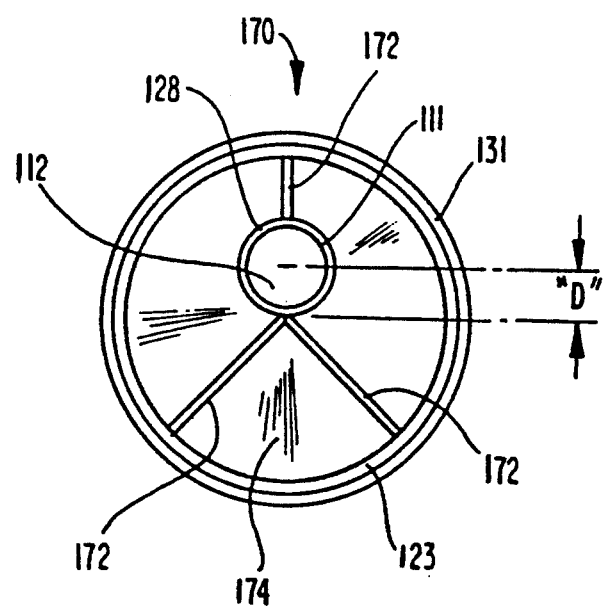
FIG. 8D is an end view of the eccentric pneumo-needle and stamped tip combination such as illustrated in FIG. 8C.

The needle subassembly 200 illustrated in FIG. 4B is organized in the following manner. Needle 28 is attachable to a graduator 29 in two different configurations, however, permitting three distinct product uses when the obturator subassembly 100 is assembled. According to a first configuration, the needle subassembly 200 and the obturator 11, which is concentric with needle 18 and graduator 29, creates an improved Veress-type needle, such as seen in FIG. 7C, that can be used independently as a product for the purpose of creating a pneumoperitoneum. The obturator tip 12 can be locked in position, thereby providing a visual and tactical indication of the position of the obturator tip 12 within the needle 28. The cap 17 on the needle 28 is removable for saline testing and improved ergonometrics. According to the second configuration, when the concentric needle assembly 200 including needle 28, graduations 29 and seal 30 are combined with trocar 21 in such a fashion that the needle 28 passes through the trocar cutting tip 25 concentrically as illustrated in FIGS. 8A and 8B, the needle 28 then acts as a pilot in combination with the trocar cutting edges 25 to provide an improved cutting action. According to the third configuration, when the needle subassembly 200 including needle 28, obturator 11, and graduator 29 are combined with trocar 21 in such a fashion that the lumen through which the obturator subassembly 100 passes, is concentric through the shaft of the needle 28 but eccentric through the graduator 29 and trocar subassembly 300, it provides an improved cutting action with respect to the cutter 25 and needle 28 as seen, for example, in FIG. 5A. Therefore, when the third configuration as seen in FIGS. 8C and 8D is used to pierce the abdominal wall, it offers coinciding cutting edges that provide continuous cutting rather than interrupted cutting as a concentric arrangement might yield.

In all configurations, the needle 28 passes through the trocar cutter 25 and extends beyond the trocar 21 with cutting edges that act as a pilot for the trocar cutter 25 as penetration of the abdominal wall proceeds from the hole 82 made by the needle 28 to an expanded hole made by the cutter 25 to the desired size of the cannula 31. When the graduator 29 is used with the trocar 21, the notches in the graduator 29 engage with the trocar latch 27 to a preset depth of penetration established by the extension of the needle tip 28 beyond the trocar cutter 25, thereby acting as a stop as the needle 28 penetrates the abdominal cavity 84 and the trocar cutter 25 comes in contact with the abdominal wall 86 as seen in FIG. 7A. Needle graduator 29 is preferably color coded to indicate depth penetration. For example, the color black indicates a pilot position of 1.5 cm, blue indicates a range of 1.5–3.0 cm and green indicates a range of 3.0–6.0 cm for simplified visual setting. The obturator subassembly 100 can be separated from the needle subassembly 200 after the abdominal cavity 84 has been entered and pneumoperitoneum has been created to provide a 1.5 mm access port, through the needle lumen to perform diagnostic and therapeutic operative procedures. A seal 30 attached to the graduator 29 restricts leakage of gas when the obturator subassembly 100 is separated and nothing else is inserted into the lumen of needle 28.

The trocar subassembly 300 illustrated in FIG. 4C is arranged in the following manner. Cutter tip 25, which preferably comprises a metal stamping containing three sharp edges as illustrated in FIGS. 6C, 6D, 8A, 8B, 8C and 8D is insert molded or mounted to a cutter support 22 which houses trocar seal 24. Trocar seal 24 restricts gas leakage when the obturator/needle subassembly 100 and 200 are withdrawn from trocar 21 and the trocar lumen is open and unobstructed. A shuttle 23 slides over cutter 25 when the trocar subassembly 300 is withdrawn from cannula 31 as result of interference with the duckbill cannula valve 34 and duckbill cannula seal 33. The shuttle 23 can slide rearwardly to expose the sharp edges of the trocar cutter 25 when that component is inserted into the cannula 31. The purpose of shuttle 23 is to prevent injury from the sharp tip of the trocar cutter 25 and to provide for the safe storage of the unit. All of the foregoing are attached to the trocar 21 at its distal end. Spring loaded latch 27 biased by spring 27a is attached at the proximal end of the trocar 21. Latch 27 has two latching positions: one which engages with the graduator 29 and locks into position with the needle 28 extending beyond the trocar cutter 25; the other position engages with the stabilizer 39 which locks into position the cannula 31 as it extends beyond the stabilizer 39. Both of the foregoing setable features are employed to control the depth of penetration of their respective elements. Needle return spring 26, housed within trocar 21, biases the needle subassembly 200 rearwardly. When latch 27 is activated, the needle subassembly 200 will move to its outermost position defined as the "pilot" position with the needle 28 extending 1.5 cm beyond the trocar cutter 25. After the needle/obturator subassembly 100 and 200 has been separated from the trocar/cannula subassembly 300 and 400 following insertion into the abdomen, a 2.5–3.0 mm access port is available for operative procedures.

An alternative embodiment of the trocar subassembly 300 would include an adjuster 42 which would increase or decrease the extension of the trocar cutter 25 beyond the distal end of cannula 31 as shown in FIG. 7D. Screw threads on the adjuster 42 permit an increase or decrease in the extension length of the trocar 21. This alternative may be necessary to permit the subassemblies to interface with current reusable cannulas, the length of which may vary according to the specifications of different manufacturers.

The cannula subassembly 400 shown in FIG. 4D is organized in the following manner. One combination of three variations can be used to create three distinct products: one, an all plastic version; second, a combination plastic cannula housing 32 and metal cannula version 31; and, third, an all metal cannula subassembly 400. The primary elements of the cannula subassembly 400 are the cannula housing 32 which interfaces with the reducer subassembly 500 and which includes snap-on rings for mounting the improved cannula duckbill valve 34, cannula duckbill seal 33, stop cock 35 to maintain pneumoperitoneum, and an axially elongated cannula tube 31. Cannula valve 34 is of a duckbill structure and is an improvement over prior art flap valves. When the improved duckbill cannula valve 34 is incorporated with the duckbill cannula seal 33, it results in less gas leakage and less resistance and interference so that a surgical instrument can pass easily through to the intra-abdominal cavity. The duckbill seal 34 has an "O" ring-shape and is formed from natural rubber so that it expands easily to allow the passage of instruments according to the size of the cannula tube 31 selected by the surgeon. The stop cock 35 is closed when in the down position and open when rotated to the up position. The rotary action of the stop cock gives the cannula subassembly a slimmer profile so that when the stop cock 35 is not in use, there is more space available in the operating arena.

The reducer subassembly 500 is illustrated in FIG. 4E. The principle purpose of the reducer subassembly 500 is to allow smaller diameter instrumentation to be used with a larger size cannula 31 and to provide an interface with the stabilizer 39 in order to control the thrusting force and depth of cannula penetration when the abdominal wall is pierced. Afterward it interfaces with the stabilizer 39 and stabilizer lock 41 to minimize the inadvertent withdrawal of the cannula 31. It also permits easy adjustable locking of the cannula 31 at the proper depth in the abdominal cavity 84 as shown in FIG. 7B. The foregoing benefits are a result of the use of reducer seal 38. The reducer subassembly housing 36 locks into position with respect to the cannula subassembly housing 32 by the interference, friction fit of O-ring 37 in conjunction with a one-half turn thread.

Figure 3:
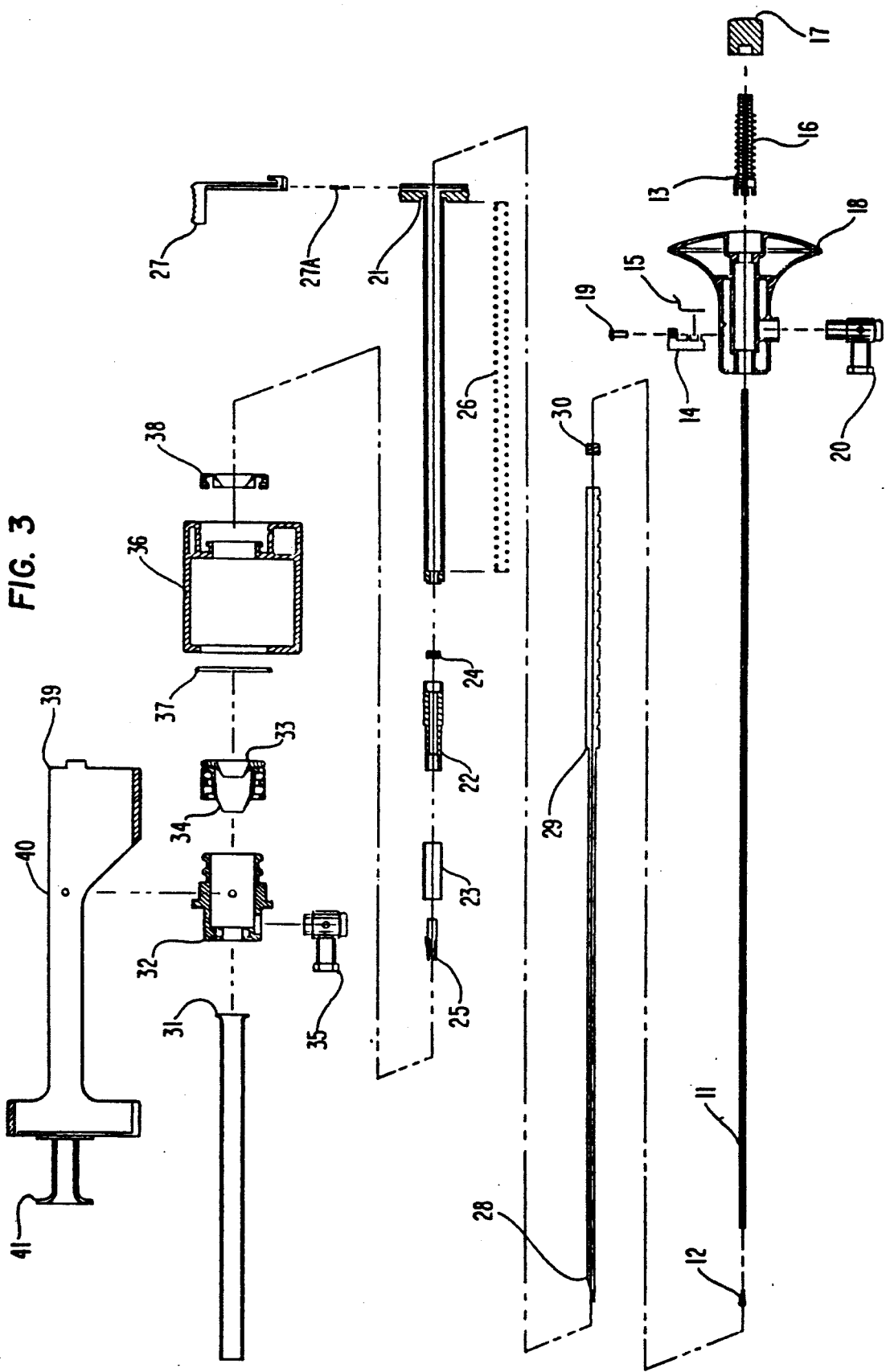
FIG. 3 is an exploded, cross-sectional view of the preferred concentric embodiment of the invention as illustrated in FIGS. 1 and 2B.

The stabilizer subassembly can be best understood by referring to FIG. 3. The principle components of the stabilizer subassembly are the stabilizer 39, latch 40 and lock 41. The stabilizer 39 attaches to the reducer housing 36 and is rotated into place and coupled at its midsection where the latch 40 engages with the reducer when the two members are axially aligned. A slot in the distal end of the stabilizer 39 allows the cannula 31, when attached to the reducer housing 36, to pass through when axially aligned in the proper orientation. The latch 40 locks an secures the reducer housing 36 to the stabilizer 39 in the desired position. In that position, the cannula 31 extends a preset distance, thereby effectively controlling the force exerted when thrusting the device into a patient to penetrate the abdominal wall. As shown in FIG. 7B, stabilizer 39 comes into contact with the abdominal wall as the cannula 31 enters the cavity 84, thereby restricting the depth to which the cannula 31 can be inserted into the cavity 84. This is an important safety feature which ensures that intra-abdominal structures are not damaged by the plunging effect that occurs when the stabilizer 39 is not present. The foregoing steps are reversed in order to remove the stabilizer 39 from the reducer housing 3 after the instrument has been inserted into the abdominal cavity when the surgeon desires only to have the cannula 31 inserted. Lock 41, attached to the distal end of stabilizer 39, engages cannula 31 and offers some resistance thereto in order to retain the cannula 31 via reducer 36 in position in the intra-abdominal cavity.

Figure 5A:
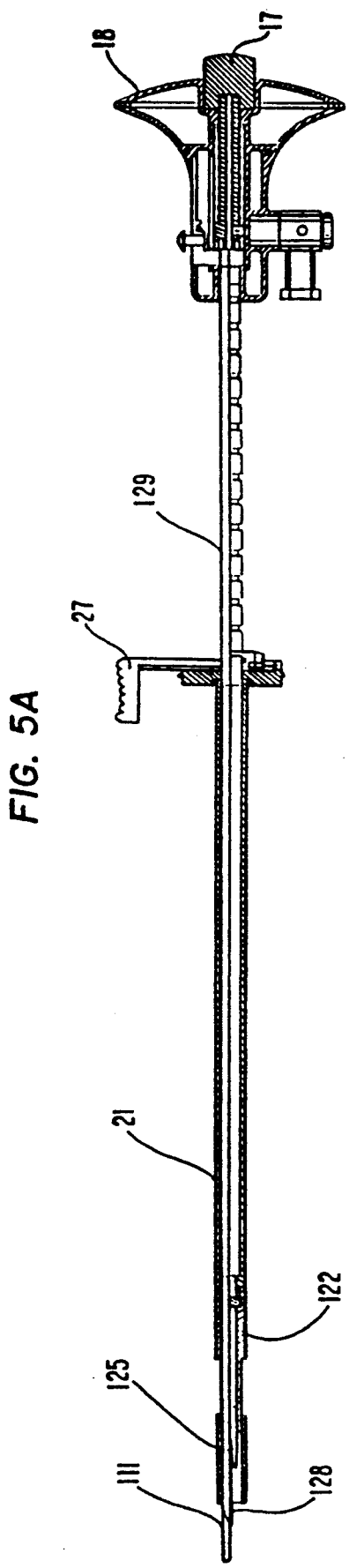
FIG. 5A is a cross-sectional view of the obturator knob, the obturator, the pneumo-needle, the trocar, and the trocar latch subassemblies combined according to the alternative eccentric embodiment of the invention such as illustrated in FIG. 2A.

The alternative eccentric embodiment 110 is illustrated in FIGS. 2A, 5A–5D and 8C and 8D. As shown in FIG. 5A, the pneumo-needle 128 and obturator 111 are eccentrically located with respect to the center of the trocar cutting tip 125. FIG. 5B illustrates the fact that the pneumo-needle and obturator tip and knob subassembly 101 are eccentrically constructed in that the obturator 111 and obturator tip 112 are eccentric with respect to the bore of the obturator knob 18. Similarly, as shown in FIG. 5C, the pneumo-needle subassembly 201 includes a pneumo-needle 128 which is eccentric with respect to the central axis of the needle graduator 129 and needle seal 130. When the obturator shaft 111 of obturator subassembly 101 is slipped inside of the shaft of the pneumo-needle 128 of subassembly 201, then both together can be slip-fitted into the shaft of trocar subassembly 301. This forms the subassembly illustrated in FIG. 5A. In this eccentric alternative embodiment 110, the trocar tip 125 and trocar cutter support 122 are eccentrically located so as to accommodate the eccentrically mounted obturator shaft 111 and eccentrically positioned pneumo-needle 128. The shaft and tip of pneumo-needle 128 are offset by a distance "D" from the center of the trocar shaft 21 in a manner that will be described subsequently with regard to the stamped tip illustrated in FIGS. 8C and 8D.

Figure 6A:
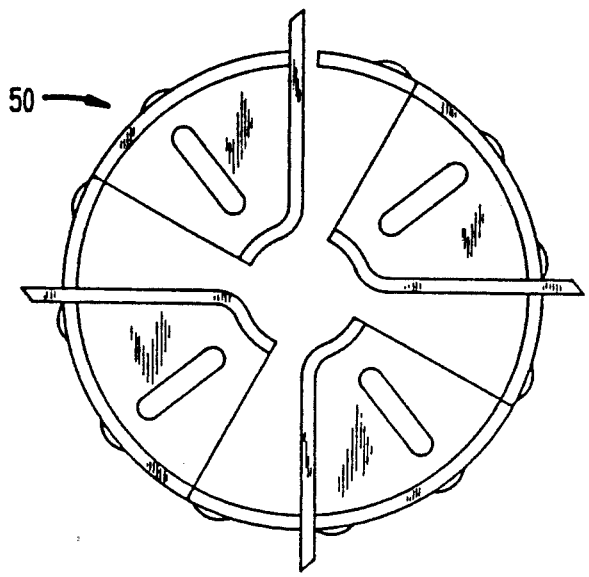
FIG. 6A is an end, elevational view of a stamped trocar tip having four cutting edges
Figure 6B:
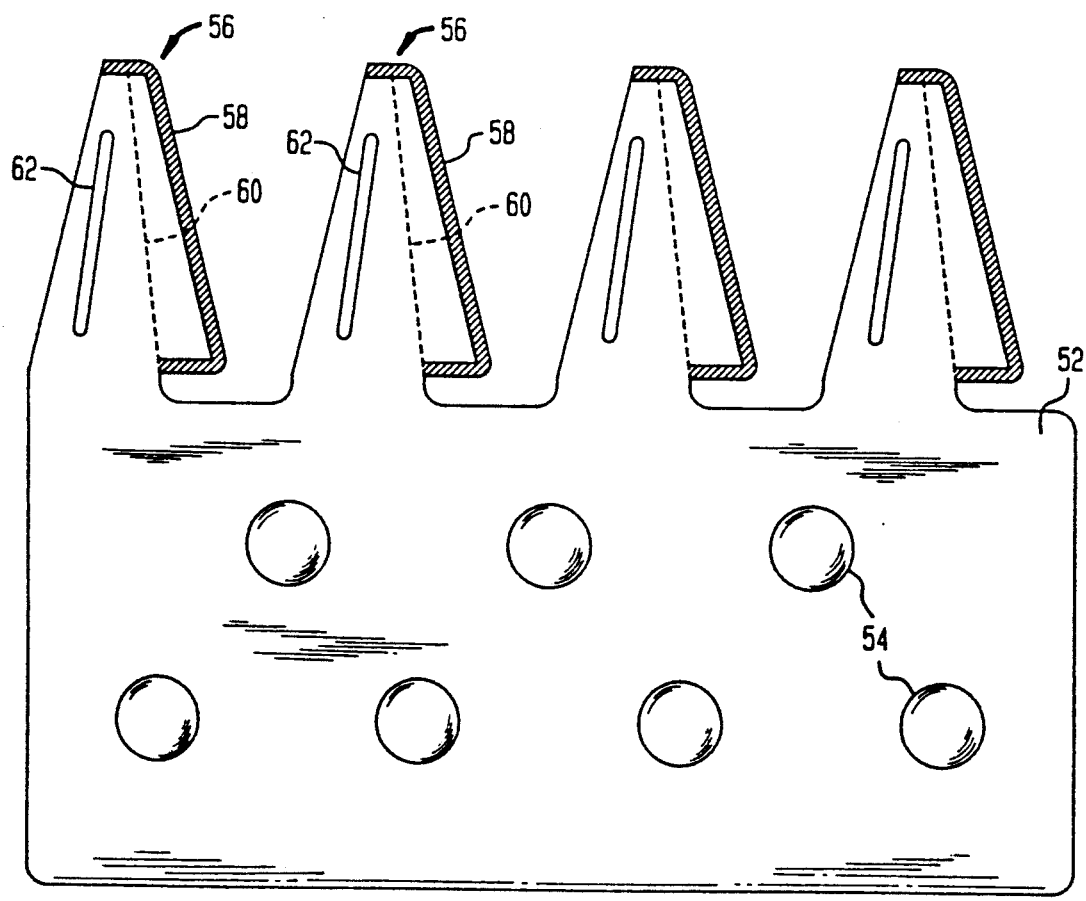
FIG. 6B illustrates a flat blank, stamped to form a four cutting edge tip of the trocar prior to its being bent and shaped to form the tip illustrated in FIG. 6A.
Figure 6C:
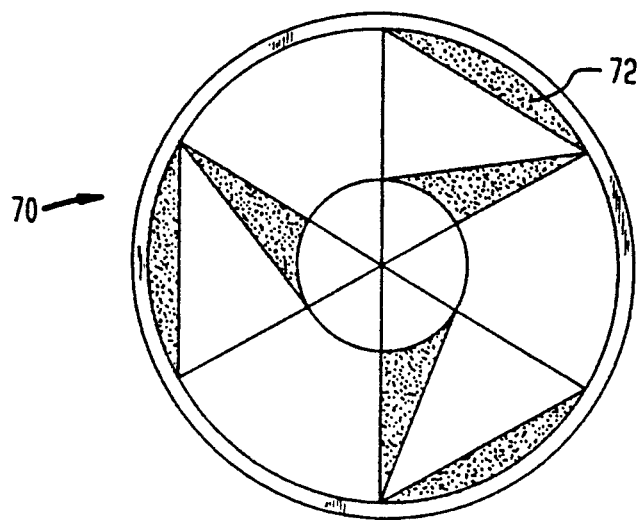
FIG. 6C is an end view of the preferred embodiment of a stamped, 3-sided trocar tip.
Figure 6D:
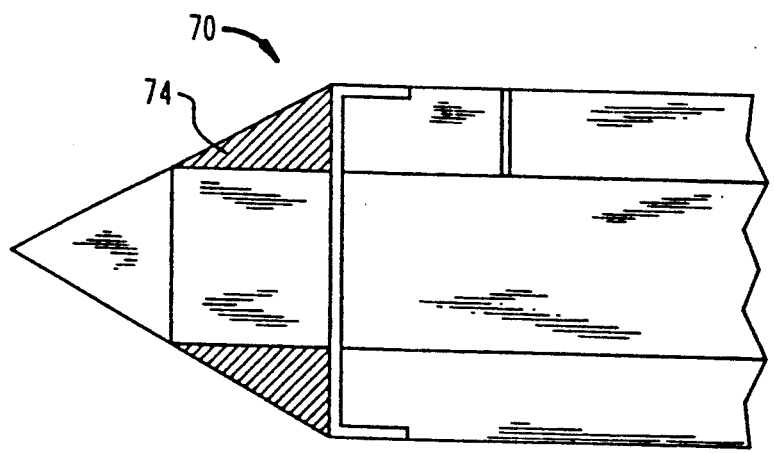
FIG. 6D is a side, cross-sectional view of the stamped, 3-sided trocar tip illustrated in FIG. 6C.
Figure 7D:
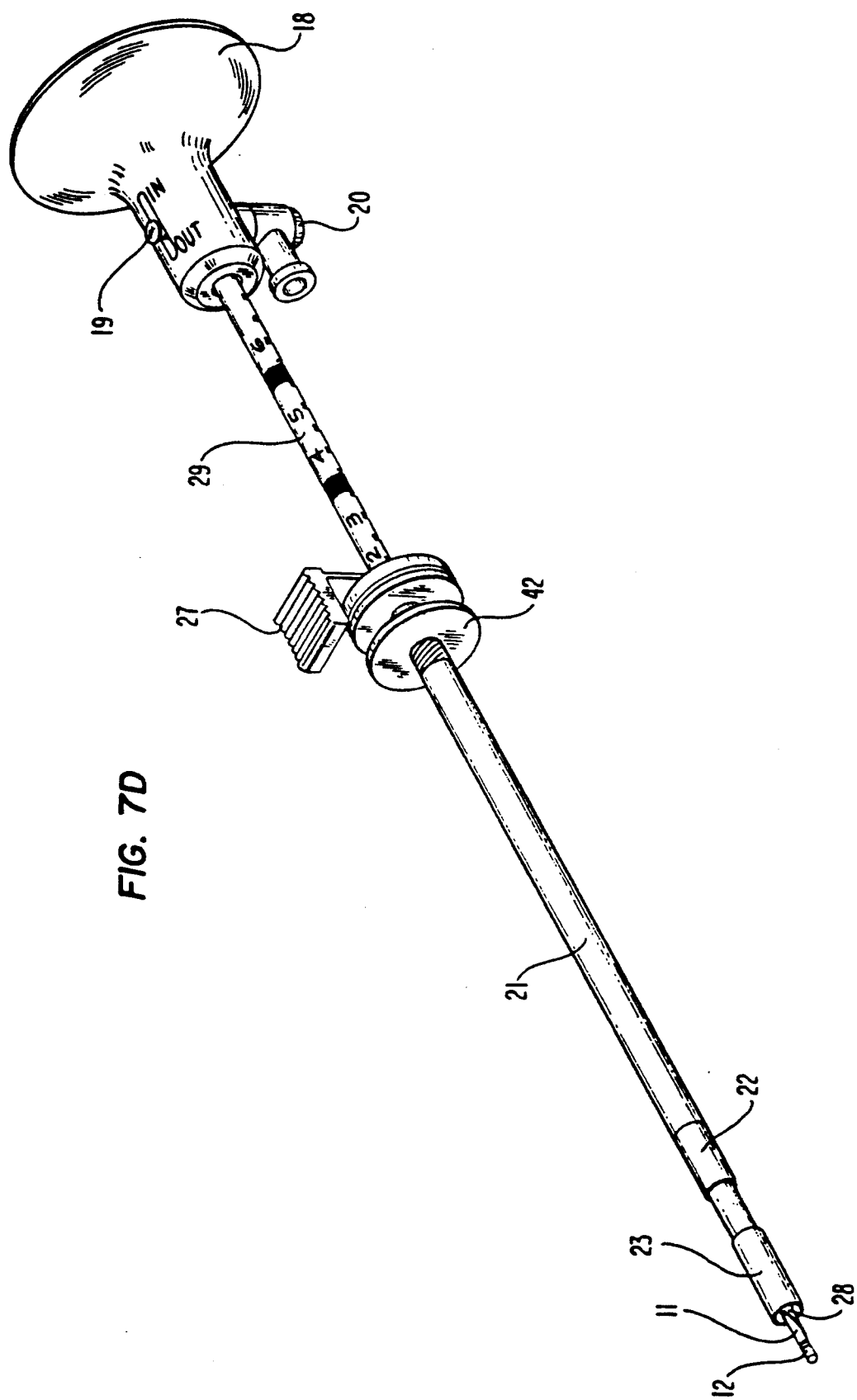
FIG. 7D illustrates the combination of a pneumo-needle, obturator tip mechanism, obturator knob, trocar and trocar latch subassembly and further including an adjuster screw, according to an alternative embodiment of the invention, employable to vary the position of the trocar cutting tip

FIGS. 6A and 6B illustrate an alternative embodiment of the invention which comprises a stamped tip for the trocar 21 such as might be employed as a substitute for the trocar cutter 25 illustrated in FIG. 1. The stamped tip 50 is formed from a flat blank 52 as shown in FIG. 6B. Blank 52 includes a plurality of welded dimples 54 that provide retention within the plastic sleeve of the trocar 21 in which it fits. Each blank 52 includes four cutting tips 56 each having coined, flat cutting edges 58. Each tooth 56 also includes a lengthwise raised boss 62 for stiffness. The rounded cutting tip 50, as shown in FIG. 6A, is formed by rolling the blank 52 in a circle and then bending each tooth around bend line 60 until it forms the shape illustrated in FIG. 6A.

The preferred embodiment of the stamped tip 70 is illustrated in FIGS. 6C, 6D, 8A and 8B. The preferred stamp tip 70 includes three teeth with cutting edges 72 which concentrically surround the tip of the pneumo-needle 28. A plastic cap or shield 74, including three corresponding slots therein, slides over the tip of the needle 28 and comes to rest in such a fashion that the leading, razor-sharp edges of the teeth 72 are exposed when assembled in the manner illustrated in FIG. 8B.

An alternative eccentric embodiment of the stamped tip 170 is illustrated in FIGS. 8C and 8D. The pneumo-needle shaft 128 has a long axis which is separated by a distance "D" from the long axis of the trocar. As seen in FIGS. 8C and 8D, the perimeter of the pneumo-needle 128 is substantially tangent to the central axis of the trocar tip 170, thereby making the offset distance "D" equal to the radius of the pneumo-needle 128 in this case. Therefore, two of the three cutting edges 172 are complete whereas one of the three cutting edges 172 is partially obliterated by the pneumo-needle 128. In FIG. 8D, the obturator tip 112, trocar cutter shuttle 123 and outer cannula 131 are also visible.

The invention 10 according to the preferred concentric embodiment 10 is operated in the following manner. Current, prior art trocar/sleeve piercing devices come in individual sizes 3, 5, 7/8, 10/11 and 12 cm. A feature of the present invention, however, is to provide two additional sizes, namely 1.5 and 2.5 mm, within each instrument regardless of size, as a result of combining the pneumo-needle 28 with the trocar 21 and cannula 31. The basic operating components of the invention 10 are the obturator 11, the Veress or pneumo-needle 28, trocar 21, cannula 31, reducer 36, stabilizer 39 and stabilizer lock 41. The components are modular and interchangeable and can be used in varying levels of assembled completeness. In addition, cannula 31 can be disposable, plastic/metal or of a reusable, all metal design. The environment in which the invention 10 is used is illustrated in FIGS. 7A-7C. Initially, the pneumo-needle 28 pierces the patient's skin 80 and creates a pilot hole 82 through which the trocar 21 and cannula 31 eventually pass. Pneumo-needle 28 reaches a preset depth within the intra-abdominal cavity 84 limited in part by the trocar cutting tip 25 coming into contact with skin 80. With pneumo-needle 28 in the position illustrated in FIG. 7A, it is possible to inflate the intra-abdominal cavity with a gas so that other procedures can be performed. With the foregoing context in mind, it is easier to understand the remaining details of the surgical procedure.

At the very beginning of the procedure, the obturator 11/pneumo-needle 28 assembly is normally preset to the "pilot" graduated position indicated by the color code black and a numerical indicator 1.5, which refers to the extension of the needle 28 by 1.5 cm beyond the trocar cutting edge 25. The eccentrically positioned "pilot" feature within the lumen of trocar 21 in conjunction with the unique trocar 25 cutting tip results in the use of lower force required to pierce the abdominal wall, thereby significantly reducing the undesirable plunging effect often associated with prior art pyramidal trocar cutting tips. Pneumo-needle 28 is locked into the graduated PILOT position by trocar latch 27. Trocar latch 27 can be depressed for unlocking purposes when it is desired to make other settings (from 1.5 to 6.5 cm) of the extension of the needle 28. Obturator 11 and its associated tip 12, which are spring loaded to cycle inward and outward, extend outwardly beyond needle 28 and are locked so that they cannot move backward into the lumen of the needle 28, thereby exposing the cutting tip of the needle 28. The cap 17 which is attached to and moves with the obturator 11, is shown in its inward position in FIG. 2. The position of the obturator 11, in either its extended or non-extended position, can be visually observed and tactilely felt in the palm of the hand of the surgeon through the movement of cap 17. Activating button 19, which is shown in its forward position, must be pressed to unlock the obturator 11 after each cycle of the obturator 11. This feature protects internal organs should the needle 28 come into contact with the organs inside the abdominal cavity 84. Button 19 is connected to and moves with obturator 11, both forward and rearward, and also provides a visual indicator to the surgeon to assist in observing the position of the obturator 11. When the obturator stop cock 20 is rotated downwardly, it assumes the closed, out-of-the-way position. Trocar 21 is inserted into the reducer 36, and the cannula 31 such that the trocar 21 and its cutting edges 25 extend beyond the distal end of cannula 31. When the trocar 21 is not being used to pierce tissue, the shuttle 23 protects the trocar 21, its cutting edges 25 and the surgeon from inadvertent injury when the trocar 21 is withdrawn from the cannula 31 and stored for further use. The shuttle slides forward or rearward as the trocar 21 passes through the duckbill cannula valve 34 and the duckbill cannula seal 33 during assembly or during withdrawal of the trocar and cannula.

Also, at the beginning of the procedure, the stabilizer 39, which can be set from 2.5 to 7.0 cm is set to 4, indicating that the tip 12 of obturator 11, extends a total of 4 cm beyond the distal end of stabilizer 39. This limits to 4 cm the total depth that the instrument (cannula 31 and the obturator tip 12 combined), can enter the abdominal wall, thereby preventing the plunging effect associated with other prior art trocar/sleeve devices. Stabilizer 39 is locked in position with respect to the reducer 36 by the stabilizer latch 40, which is activated when it is desired to change the depth of penetration of the cannula 31 (for example, in the range of from 2.5 to 7.0 cm). Stabilizer 39 is interlocked with pneumo-needle 28 in the pilot position via trocar latch 27 which must be depressed to release needle 28. The purpose of the safety interlock is to ensure that the needle 28, which is sprung outwardly from trocar 21 by needle return spring 26, is returned to the pilot position when the trocar latch 27 is activated to set cannula 31 to the depth of penetration desired. This ensures that needle 28 is always in the pilot position rather than extending greater than 1.5 cm when the cannula 31 is thrust through the intra-abdominal cavity wall. Once penetration of the intra-abdominal wall is complete, stabilizer lock 41, which is attached to the distal end of stabilizer 39, is activated to create a secure lock of the position of the stabilizer 39 with respect to the intra-abdominal wall as shown in FIG. 7B, thereby preventing the inadvertent withdrawal of the cannula 31 which is locked to the stabilizer 39 by reducer 36. The location of the cannula 31 within the intra-abdominal cavity can be repositioned without unlocking stabilizer 39 by simply releasing stabilizer latch 40 and repositioning the cannula 31, and reducer 36, within stabilizer 39, thereby affording the surgeon a level of control not currently available with other prior art devices which generally cannot be adjusted once locked to the intra-abdominal wall.

The first step in the procedure is for the surgeon to make a determination of the patient's abdominal wall thickness, either by a pinch test or by knowledge of the relatively accurate historical data in the literature based upon samplings of many patients of the same size and shape. In general, for thin patients, penetrations of 2-3 cm are sufficient, whereas for heavier patients, penetrations of 3-6 cm are normal. After making the determination of depth of penetration, the surgeon depresses the trocar latch 27, thereby setting the graduator 29, to the desired penetration depth either by using the color code method (blue for thin patients/green for heavier patients) or by setting the graduator to the numeric position indicators for wall thickness (2-6 cm). A visual observation of the extension of the pneumo-needle 28 also gives the surgeon an estimate of the penetration desired. In setting the graduator 29, the surgeon must overcome the spring force of the needle return spring 26, which biases the pneumo-needle 28 outwardly and, in conjunction with the trocar latch 27, locks the needle 28 in the desired position. The surgeon then selects the surgical site, performs other normal preparations, observes all of the above instrument settings and makes alterations, if necessary, prior to proceeding.

At the beginning of the penetration step, the surgeon grasps the knob 18 such that the obturator button 19 can be operated with the index finger of one hand. With the other hand, the surgeon grasps the abdomen elevating it to an optimal position. Then the surgeon, after depressing button 19 which releases the obturator lock 15, positions the obturator tip 12 at the surgical site and begins to thrust forward. While thrusting forward, the surgeon removes his or her index finger from the button 19 which begins to move rearwardly. Obturator 11 will continue to move inward within the lumen of needle 28. While this happens, button 19 will be observed to move rearward and the cap 17 will be tactilely felt in the palm of the surgeon's hand as it moves, giving feedback to indicate that the obturator 11 is in its rearward position and the needle 28 is exposed and cutting through the abdominal wall. The surgeon continues to thrust until the visual indicators, the cap 17 and button 19, move to their forward positions at which point an audible click is heard which indicates that entry has been achieved, all of which occurs just prior to the surgeon feeling the resistance of the cutting edge 25 of the trocar 21 coming into contact with the skin 80 as shown in FIG. 7A. At that point, the surgeon discontinues the thrusting step. The foregoing structure substantially eliminates the plunging effect associated with other trocar/sleeve devices. Generally, the cutting edge 25 of trocar 21 will penetrate approximately 0.5 cm at the time that the pneumo-needle 28 makes its pilot entry. After the initial pilot hole has been formed, the surgeon releases his or her grasp of the abdominal wall so that both hands are free to operate and steady the instrument in a generally perpendicular, upright position. If the surgeon wishes to test the entry wound, cap 17 can be removed and a standard saline test made. When the surgeon is assured that the cavity has been entered, cap 17 can be returned and the rotary stop cock 20 is rotated upwardly, thereby opening a passageway through the obturator 11 to the cavity 84. An insufflator hose is then attached to the stop cock 20 and the cavity 28 inflated. When this portion of the procedure is completed, stop cock 20 is rotated downwardly to its closed position and the insufflator hose is removed. The surgeon then tests the depth of full penetration of the instrument 10. Again, the estimated wall thickness, now confirmed by the initial penetration of the needle 28, is used to set the position of the stabilizer 39. Using the thumb and index finger of one hand, the thumb is placed on the reducer 36 and the index finger on the trocar latch 27 so that it can be depressed. The thumb of the other hand is placed on the stabilizer latch 40 and the index finger of the other hand is placed o the opposite side in a pinching fashion to depress trocar latch 27, holding it there until needle 28 returns to the pilot position so that the stabilizer latch 40 can be squeezed, thereby permitting the stabilizer 39 to slide to the desired setting. Stabilizer lock 41 moves along with the stabilizer 39 to the desired setting as previously described. With a firm grasp on knob 18, the surgeon thrusts the instrument through the intra-abdominal wall following the pilot hole created by needle 28, and obturator 11, with the obturator tip 12 extended, in its forward position until resistance is felt from the stabilizer 39 contacting the skin 80, to protect organs from the sharp point of the needle 28 should the needle 28 come in unintentional contact with organ structures 86. Needle 28 passes eccentrically through the trocar cutting edge 25 so that the edges of the needle 28 and the cutting edges of the trocar tip 25 coincide, i.e. are flush with respect to each other at the center point of the lumen of the cannula 31. This structure results in the use of a lower force to pierce the skin 80 and the abdominal wall than would result if the needle 28 passed through the dead center of the axis of the trocar 21. The eccentrically located pilot hole, which results in the use of lower piercing force when used in conjunction with the depth limiter of stabilizer 39, minimizes, if not eliminates, the plunging effect associated with other prior art piercing devices. The plunging effect is further minimized by the stabilizer contacting the abdominal wall, thereby ceasing forward thrust.

After the piercing step is complete, the stabilizer 39 is locked into position with respect to the abdominal wall by the stabilizer lock 41 as shown in FIG. 7B. The cannula stop cock 35 is then rotated to the open position and an insufflator tube is attached so that cavity pressure can be maintained. The surgeon is now ready to perform standard, well known procedures.

Depending upon the diameter of the operative instruments used, the surgeon has the following options:

For a 1.5 mm access, the obturator 11 only is removed and the lumen of needle 28 provides access. Needle seal 30 prevents gas leakage. For a 2.5 mm access, only the obturator 11 and needle 28 are removed, with the lumen of trocar 21 providing access. Trocar seal 24 prevents gas leakage. Removing the obturator 11, needle 28 and trocar 21, provides access through the cannula 31. As the trocar 21 is removed, the shuttle 23, by way of interaction with cannula seals 33 and 34, slides forward to cover the sharp cutting edges 25 of trocar 21. Duckbilled cannula valve 34 and seal 33 prevent gas leakage and, because of their unique design, are less restrictive and less prone to interfere as the operative instruments pass through to the abdominal cavity. If a large cannula 31 is used in place of a small cannula 31, the reducer seal 38 is interchanged to provide the appropriate diameter with respect to the instrument used in order to prevent gas leakage. If the surgeon prefers just the cannula 31 to remain in place, the stabilizer lock 41 can be detached from the stabilizer 39 which remains with the cannula 31 in the abdominal wall. When the cannula 31 is properly positioned in the abdominal cavity, the stabilizer 39 can be removed from the reducer 36 by depressing stabilizer latch 40 and rotating the stabilizer 39 45° with respect to the latch position which is midway along the length of the stabilizer 39 so that the cannula 31 can pass through the slot provided in the stabilizer 39. At the same time, the surgeon, while grasping the cannula tube 31 in one hand, slides the stabilizer 39 beyond the proximal end to separate it from the reducer 36.

Because of the interchangeable, modular nature of the invention, it is possible to reassemble the obturator 11, needle 28 and trocar 21 for use with another cannula 31 or reducer 36 or stabilizer 39 including stabilizer lock 41, of any size, to make additional punctures. Other combinations are also possible. The interchangeability feature provides for safe penetration with each and every puncture after which the components can be used in a cost effective manner. In particular, and based upon the surgeon's preference, further cost effectiveness can be achieved by reusing the obturator 11, needle 28 and trocar 21 with a reusable cannula/reducer by making respective elements either disposable or reusable and either of plastic or metal.

The versatility of the invention is further extended by using the obturator 11, needle 28 and trocar 21 assembly with existing reusable cannulas currently available. Cannula tubes are available in many different lengths. Since it is necessary for the cutting edge 25 of trocar 21 to extend beyond the cannula tube 31, the invention 10 is provided with an adjuster screw 42 that can be set to achieve the desired position of the cutting edge 25 relative to the length of the cannula tube 31 chosen as shown in FIG. 7D.

The invention just described provides greater safety than prior art trocar devices and yet achieves a significant increase efficacy, cost effectiveness and convenience. In particular, it has the following special advantages over the prior art. First, a lower force is required to pierce with the trocar, thereby decreasing the chance of unnecessary internal wounding to the patient. Second, the spring-loaded obturator complies with current safety standards and provides additional safety to the patent. Third, the one cycle locking safety mechanism has a low return spring force which is safer and more efficacious because a lower spring force is more likely to penetrate the peritoneum. Fourth, the combination of visual, audible and tactile indicators to the surgeon adds greater safety by providing the surgeon with better overall awareness and control of the instrument. Fifth, the addition of 1.5 mm and 2.5 mm access ports are more versatile and time saving than prior art devices. Sixth, the modular built-on features are advantageous because they provide the surgeon, nurse and purchasing agent with more cost effective and flexible choices that can permit the user to customize and mix the elements that comprise the invention. Seventh, the depth penetration limiters add additional safety and control to the instrument. Eighth, the abdominal locking stabilizer which includes the capability of repositioning the cannula, provides for greater flexibility during surgical procedures. Ninth, though not necessarily last, the cannula seals and valves provide superior gas leak prevention.

The above description can also be found in my co-pending U.S. patent application Ser. No. 08/010,769 filed Jan. 29, 1993.

The following preferred embodiment 600 of my invention is an improvement thereover which increases the control that a surgeon has over the positioning of the trocar and cannula as they travel down the shaft of the pneumo-needle. The preferred concentric embodiment of the present invention 600 is illustrated in perspective view in FIG. 9A and in a cross-sectional view in FIG. 9B. As seen from the exterior, the preferred embodiment 600 includes an obturator knob 602, an obturator housing cap 604, an obturator activating button 606, an obturator stop cock 608, a pneumo-needle 610, needle graduation 646, needle retainer 612, needle retainer latch 614, needle retainer cannula stop 616, reducer housing 618, needle retainer reducer housing lock 620, stop cock 622, cannula 624, cannula housing 626, trocar cutting tip 628, cutting tip 630 of needle 610, obturator 632 and obturator tip 634.

The obturator sub-assembly 100 is essentially identical to the embodiment illustrated in FIG. 4A and previously described.

Figure 9B:
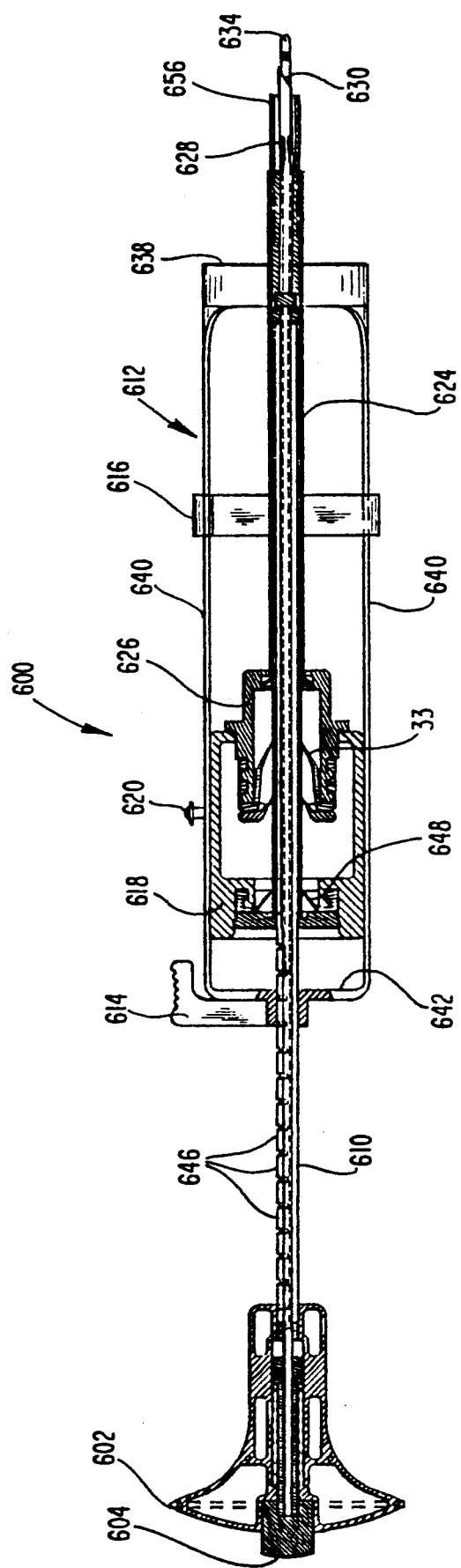
FIG. 9B is a cross-sectional view of the preferred embodiment of the combined, concentric pneumo-needle and trocar apparatus illustrated in FIG. 9A.
Figure 10A:
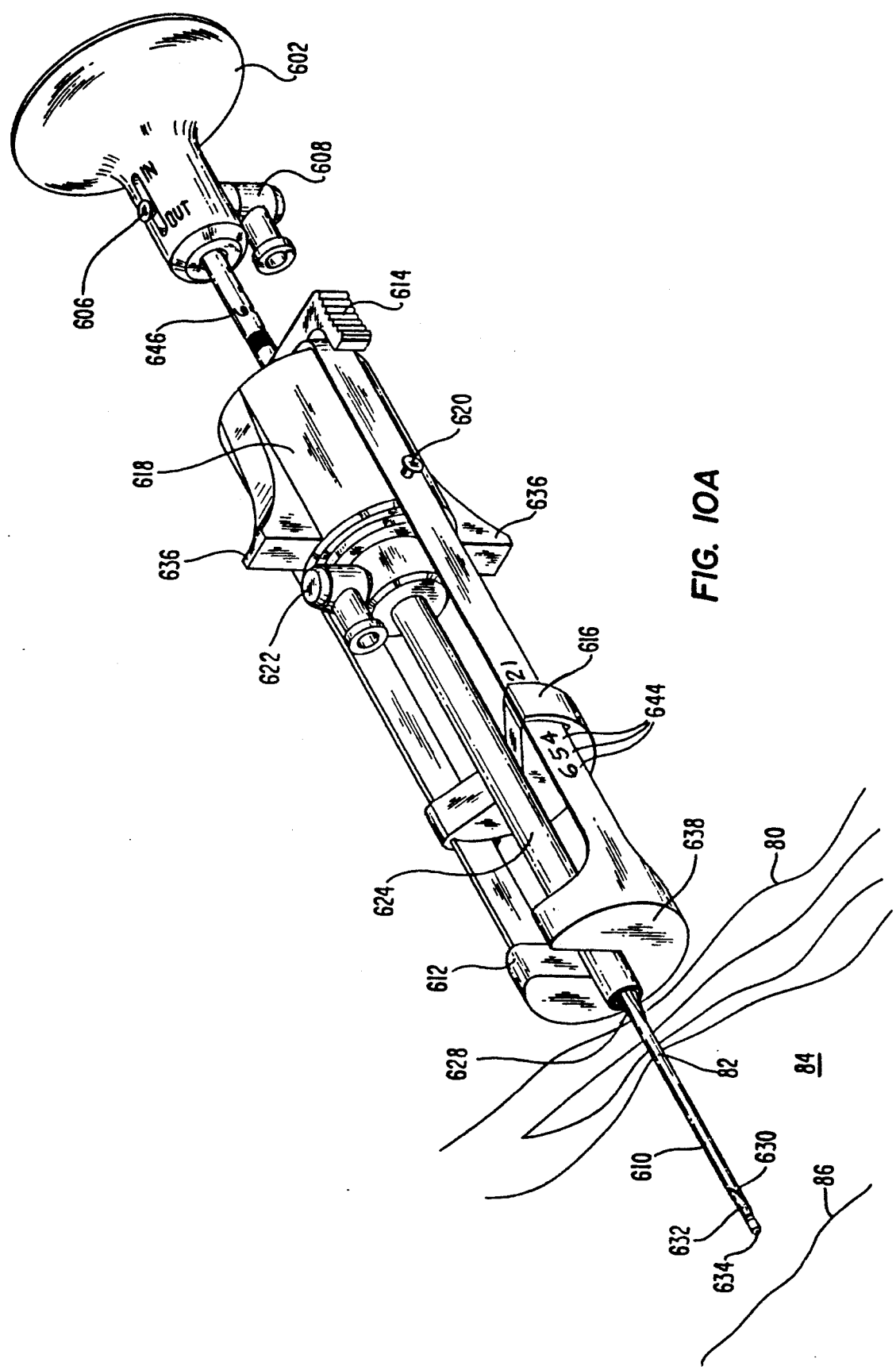
FIG. 10A illustrates an initial step in the use of the combined pneumo-needle/trocar/needle retainer according to the preferred embodiment of the invention illustrated in FIG. 9A in which the pneumo-needle has pierced the abdominal wall of the patient and has been thrust to full depth inside the abdominal cavity.
Figure 10B:
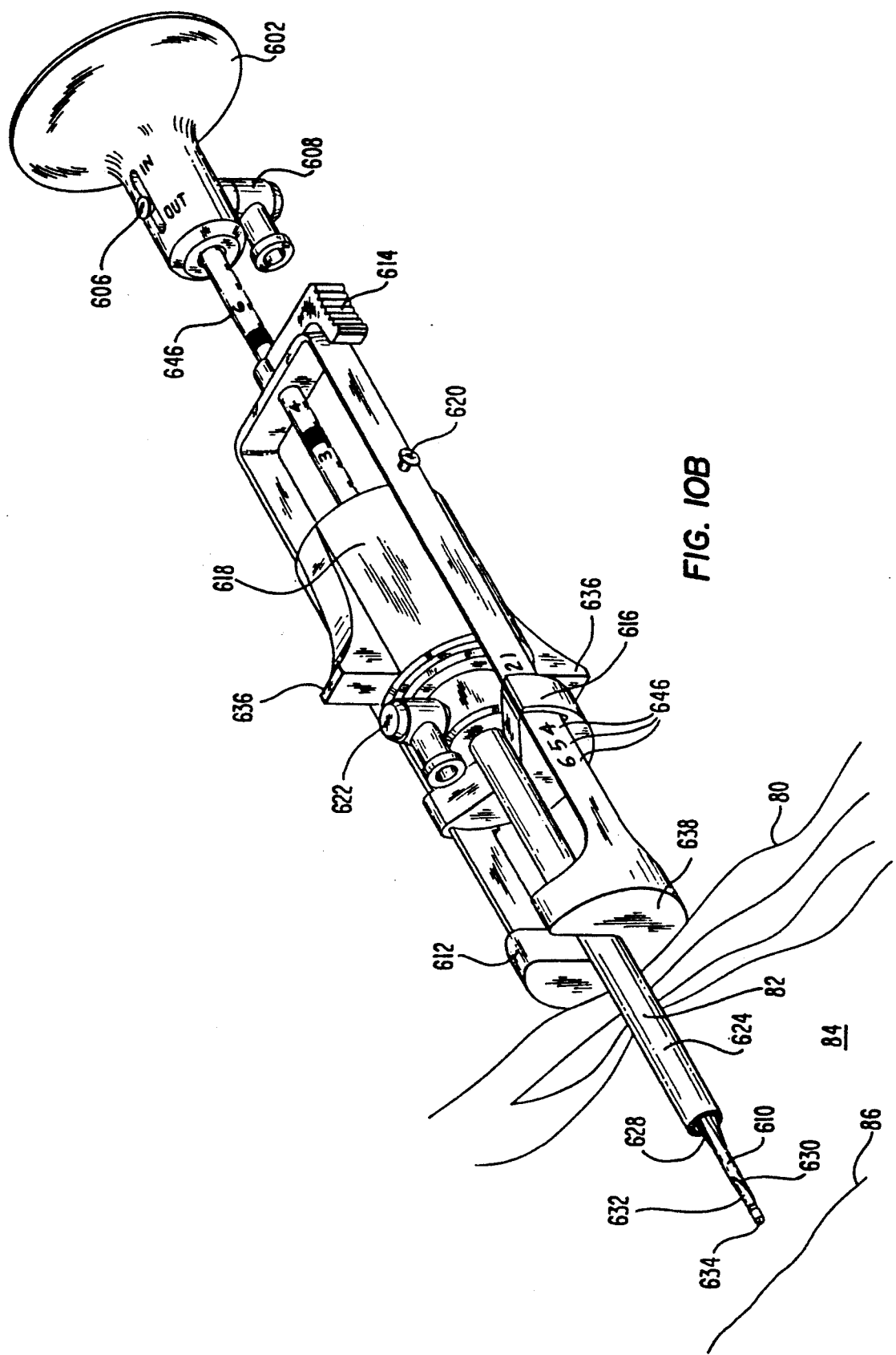
FIG. 10B illustrates a subsequent step in the use of the preferred embodiment of the invention illustrated in FIG. 9A, wherein the trocar and cannula follow the pneumo-needle to a precise depth and location as controlled by the cannula stop mechanism.

The needle sub-assembly 200 a illustrated in FIG. 4B is essentially identical to the equivalent structure 610 in FIGS. 9A, 9B, 10A, and 10B. The needle sub-assembly 200 illustrated in FIG. 4B can be used in multiple configurations to achieve benefits previously described. In the preferred embodiment of the invention 600, the concentric needle passes through the trocar cutting tip 628 and extends beyond the trocar 650. The cutting edge 630 and the needle body 610 act as a pilot for the trocar cutting tip 628, as seen in FIGS. 10A and 10B, as penetration of the abdominal wall proceeds from the pilot hole 82 made by needle 610 to an expanded hole made by the trocar cutting tip 628 to the desired size of the cannula 624. In the preferred embodiment 600, the needle graduations 646 are used in conjunction with the needle retainer 612 and needle retainer latch 614 to set the depth of penetration of the needle 610 by establishing the extension of the needle tip 630 beyond the trocar cutting tip 628. Because the needle 610 is locked by latch 614 with respect to needle retainer 612, it is impossible for the cutting tip 630 of the needle to extend any further than the front face 638 of the needle retainer 612. All other needle setting features and functions are essentially the same as in the previously described embodiments 10 and 110.

Figure 9E:
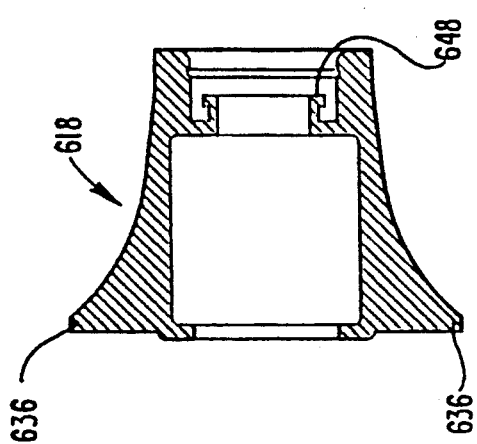
FIG. 9E is a cross-sectional view of the reducer housing sub-assembly and reducer seal according to the preferred embodiment of the invention illustrated in FIG. 9A.
Figure 9D:
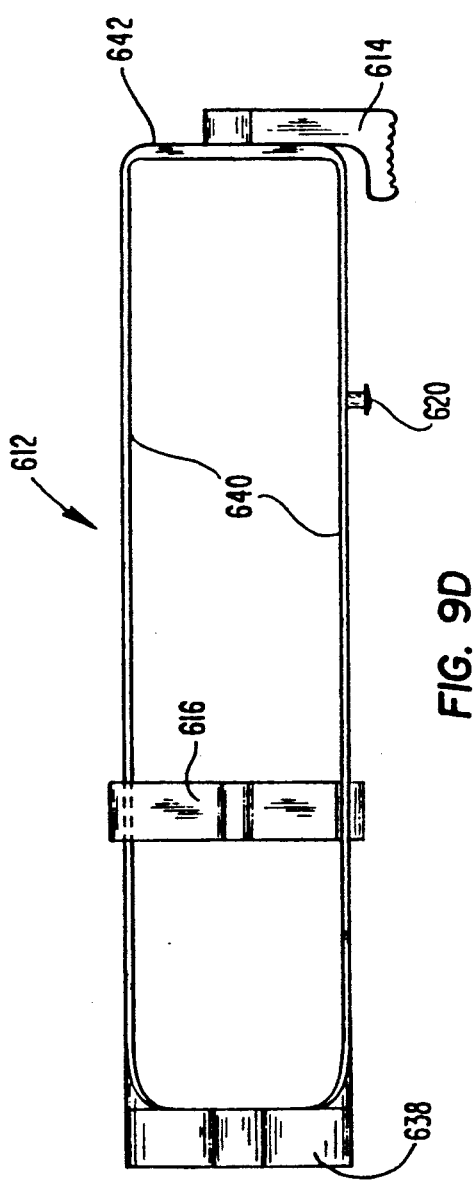
FIG. 9D is a top plan view of the needle retainer sub-assembly according to the preferred embodiment of the invention illustrated in FIG. 9A.
Figure 9F:
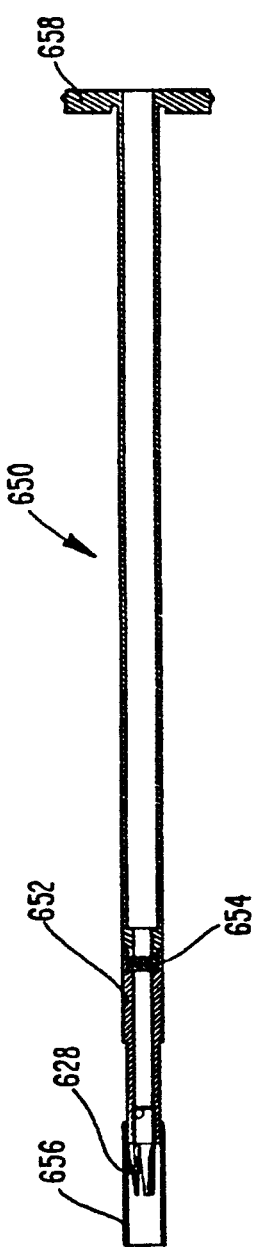
FIG. 9F is a cross-sectional view of the trocar sub-assembly according to the preferred embodiment of the invention illustrated in FIG. 9A.

The trocar sub-assembly 650 illustrated in FIG. 9F is similar to the trocar sub-assembly 300 illustrated in FIG. 4C with the exception that the trocar latch 27 and spring 27A have been removed and relocated to rear face 642 of the retainer 612 as shown in FIGS. 9A, 9B, 9C and 9D. The previous needle return spring has been deleted, to create the alternative embodiment of the trocar 650. This achieves an additional benefit. According to the preferred embodiment 600, the needle graduations 646 engage with the needle retainer 612 through the needle latch 614. Because the needle latch 614 engages the graduations 646, it naturally limits the depth of penetration of needle 610 during the initial thrusting step because the front face 638 of the needle retainer naturally meets resistance when it comes into contact with the skin 80 on the abdominal wall. This prevents further penetration of the needle tip 630 beyond a preset distance into the abdominal cavity 84. In this arrangement, the needle retainer 612 rigidly holds the needle body 610 which then acts as a true pilot over which the trocar 650 passes. Similarly, the depth of penetration of the cannula 624 which surrounds the trocar 650 is controlled during the subsequent thrusting step by the needle retainer cannula stop 616 which prevents the cannula 624 and the trocar tip 628 from extending any further than the front face 638 of the needle retainer 612. Once safe entry of the needle 610 has been achieved, it acts as a pilot over substantially all of its extended length for the trocar 650 and the cannula 624. This substantially increases the safety of the surgical procedure because the ultimate depth of the needle is precisely controlled and the path of the cannula 624 and trocar cutting tip 628 through the pilot hole is absolutely ensured as is the final bottoming depth of the trocar cutting tip 628

Another benefit of the invention 600 is that it provides the surgeon with a choice of intra-operative procedures at the time of safe needle penetration. The surgeon can elect either to create pneumo-peritoneum at the time of complete needle penetration or elect to proceed, without pneumo-peritoneum, to direct cannula insertion, wherein the trocar 650 and the cannula 624 are inserted directly into the abdominal cavity prior to creating pneumo-peritoneum, which, according to prior art case studies, produces superior results. While benefits are known, surgeons have traditionally been reluctant to elect direct insertion, without pneumo-peritoneum, because present prior art instruments do not lend themselves this technique because of the difficulty of their use and control.

The cannula sub-assembly 400 illustrated in FIG. 4D is substantially identical to the cannula 624 according to the preferred embodiment 600 of the invention.

The reducer housing sub-assembly 618 according to the preferred embodiment 600 of the invention is illustrated in FIG. 9E. The principle of the reducer housing sub-assembly 618 is similar to the purpose of reducer housing 36 illustrated in FIG. 4E, and that is to permit smaller diameter instrumentation to be used with a larger size cannula such as cannula 31 illustrated in FIG. 4D or cannula 624 illustrated in FIG. 9A. Reducer housing 618 includes a reducer seal 648, similar to seal 38 of reducer sub-assembly 500. However, in addition, reducer housing sub-assembly 618 also includes a pair of pusher means or wings 636. Pusher wings 636 can be grasped by the thumb and fingers of the surgeon and used to push or advance the cannula 624 and trocar tip 628 into the abdominal cavity 84. Reducer housing sub-assembly 618 also provides an interface with the needle retainer 612 in order to control the thrusting force and depth of penetration of the trocar tip 628 and cannula 624 when the abdominal wall 80 is pierced as illustrated in FIG. 10B. The reducer sub-assembly housing 618 locks into position with respect to the cannula sub-assembly 624 by the interference, friction fit of an O-ring such as O-ring 37 illustrated in FIG. 2B in conjunction with a one half turn thread.

The needle retainer sub-assembly 612 is illustrated in detail in FIGS. 9C and 9D. The principal components of the needle retainer sub-assembly 612 include needle latch 614, cannula stop 616, a front face 638, a pair of side arms or sections 640 and a rear face 642. Cannula stop graduations 644 assist in selecting the depth of penetration of the trocar 628 and the cannula 624. Reducer housing lock 620 locks the reducer housing sub-assembly 618 with respect to the needle retainer 612 in its furthest withdrawn position. Needle retainer 612 attaches to the reducer housing 618 by rotation and is coupled at its mid-section by spring loaded latch or lock 620 which engages the reducer housing 618 when it is axially aligned with the needle retainer 612. A V-shaped slot in the cannula stop 616 supports the cannula 624. The slot in the cannula stop 616 is aligned with a slot in the front face 638 of the needle retainer 612 so that the cannula 624 is coaxial and properly aligned with respect to the reducer housing 618. Cannula stop 616 is setable with respect to needle retainer 612 from 1.0 to 6.0 cm and indicates the desired extension distance of the trocar cutting tip 628 beyond the distal face 638 of the needle retainer 612. After the cannula stop 616 has been set to the desired position, the surgeon pushing on the pusher wings 636 of the reducer housing 618 can push the cannula 624 and the trocar cutting tip 628 to a specific depth of penetration as illustrated in FIG. 10B. This is an important safety feature which assures that intra-abdominal structures are not damaged by the plunging effect that occurs with prior art devices which cannot adequately control the location and depth of penetration of the needle 610, trocar cutting tip 628 and the cannula 624.

Needle retainer 612 is removed from the reducer housing 618 by reversing the steps previously described after the cannula 624 has been inserted into the abdominal cavity 84.

The preferred embodiment 600 of the invention is operated in the following manner. At the very beginning of the procedure, the obturator 632, pneumo-needle 610 and needle retainer 612 assembly are normally set to the graduated position indicated by the color black and a numerical indicator 1.5, which refers to the extension of the needle point 630 by 1.5 cm beyond the trocar cutting tip 628. The concentrically positioned needle 610 within the lumen of trocar 650 in conjunction with the unique trocar cutting tip 628 results in the use of lower force required to pierce the abdominal wall 80. Pneumo-needle 610 is locked in position by needle retainer latch 614. Needle retainer latch 614 can be unlocked by depressing it or manipulating it with the finger so that other settings can be made. The graduations 646 on the pneumo-needle 610 permit a range of between 1.5 to 6.5 cm of extension of the needle cutting tip 630 beyond the trocar cutting tip 628.

The trocar 650 is inserted into the reducer housing 618 and the cannula 624 in such a way that its cutting tip 628 extends beyond the distal end 638 of cannula 624. When trocar 650 is not being used to pierce tissue, a shuttle 656, shown in FIG. 9F, covers the trocar cutting tip 628 in the same manner that shuttle 23 covers the cutting tip 25 of the embodiment 10 illustrated in FIG. 2B. Shuttle 656 protects the trocar cutting tip 628 from damage and also prevents the surgeon from inadvertently hurting himself or herself when the trocar 650 is withdrawn from the cannula 624 and stored for subsequent use. Shuttle 656 slides forward or rearward as the trocar 650 passes through the duckbill cannula valve 34 (see FIG. 2B) and the reducer housing seal 648 during assembly or during withdrawal of the trocar 650 from cannula 624.

At the beginning of the procedure, the reducer housing 618 is in its most rearward position abutting the rear face 642 of the needle retainer 612 as illustrated in FIG. 9A. Reducer housing 618 can slide forward or rearward with respect to the needle retainer 612 to a position established by the selectively setable cannula stop 616 which determines the distance that the cannula 624 extends beyond the distal face 638 of needle retainer 612. The depth of penetration of the cannula 624 is determined by the setting of the cannula stop 16 at one of the graduations 644 of between 0 to 6.0 cm. Reducer housing 618 is lockable in position with respect to needle retainer 612 by means of needle retainer lock 620 which is activated when it is desired to push the reducer 618 by means of finger manipulatable wings 636 and cannula 624 into the abdominal cavity 84 during the insertion process. Needle retainer 612 is interlocked with respect to pneumo-needle 610 at a 1.5 cm position as established by graduations 646 and needle retainer latch 614 which must be depressed in order to release needle 610.

The initial step in the insertion procedure is for the surgeon to make a determination of the patient's abdominal wall thickness, either by a pinch test or by knowledge of the relatively accurate historical data in the literature based upon samplings of many patients of the same size and shape. In general, for thin patients, penetrations of 2-3 cm are sufficient, whereas for heavier patients, penetrations 3-6 cm are normal. After making the determination of depth of penetration, the surgeon depresses the needle retainer latch 614, thereby setting the graduator 646 to the desired depth either by using a color code method (blue for thin/green for heavier patients) or by setting the graduator 646 to the numeric positions indicated for wall thicknesses based upon historical data (2-6 cm normally). A visual observation of the extension of the pneumo-needle 610 also gives the surgeon a fairly reliable estimate of the penetration desired. The surgeon then activates and sets the cannula stop 616 similarly either by color code or by numerical position as established by graduations 644. This is similar to the manner in which the surgeon gauges the graduation 646 of the needle 610. Typically, if the needle graduations 646 are set to a predetermined depth by latch 614, then the cannula stop 616 is also set to the same predetermined depth. For example, if the desired needle graduator setting 646 is at 3.0 cm, then the cannula stop 616 is also set to 3.0 cm. This governs the depth of penetration of the trocar 650 and cannula 624 so that the trocar 650 and cannula 624 pass substantially down the entire length of the pneumo-needle 610 to essentially the exact same depth of penetration as the tip 630 of the pneumo-needle 610. Penetration of the pneumo-needle 610 takes substantially less effort than penetration of the trocar 650 and the associated cannula 624. It is then much easier for the surgeon to push the trocar 650 and the cannula 624 down the shaft of the pneumo-needle 610 to precisely the correct depth and location without the risk of injury to the patient.

Initially, the surgeon grasps the knob 602 such that the obturator button 604, seen in FIG. 9B, can be operated with the index finger of the same hand. With the other hand, the surgeon grasps the abdomen, elevating it to an optimal position. Then the surgeon, after depressing release button 606, which releases the obturator lock 15 (see embodiment 10 and FIG. 2B), positions the obturator tip 634 at the surgical site and begins to thrust forward. While thrusting forward, the surgeon removes his or her index finger from button 606 which begins to move rearwardly. Obturator tip 634 will continue to move inward within the lumen of pneumo-needle 610. While this happens, button 606 will be observed to move rearwardly and the cap 604 will be tactilely felt in the palm of the surgeon's hand as it moves, thereby giving additional feedback to the surgeon to indicate that the obturator tip 634 is in its rearward position and that the cutting tip 630 of the needle 610 is exposed and cutting through the abdominal wall 80. The surgeon continues to thrust until the visual indicators, including the cap 604 and button 606 move to their forward position at which point an audible click is heard which is created by the obturator lock 15 snapping into and engaging obturator 632. This happens after entry has been achieved so that the obturator tip 634 protects the patient from further penetration by the cutting tip 630 of needle 610. All of this typically occurs just prior to the surgeon feeling the resistance of the needle retainer 612 acting as a penetration depth limiter as contact is made with the abdominal wall 80 as illustrated in FIG. 10A. The surgeon, at that point, discontinues the initial needle thrusting step. The foregoing structure substantially eliminates the plunging effect associated with other prior art trocar/sleeve devices and is, therefore, far superior in safety in that it has less of a tendency to strike and damage internal organs.

After the initial pilot hole has been formed by pneumo-needle 610, the surgeon releases his or her grasp of the abdominal wall 80, thereby making both hands available for operating the apparatus 600. At this point, the pilot needle 610 is now locked in place and restricted from further penetration by the contact of the leading face 638 of needle retainer 612 with the abdominal wall 80. If the surgeon wishes to test the entry wound, a standard saline test can be made through cap 604. Once entry is achieved, the needle 610 acts as a true pilot for the trocar 650 and cannula 624 to follow, all of which provides the surgeon a high degree of confidence that the subsequent major penetration step will be injury free. This is extremely important, in that, at this time of the procedure, the surgeon can make the decision to perform the insufflation step before proceeding with further penetration by the trocar 650 and cannula 624 or, if he or she chooses, may with confidence decide to continue the direct insertion technique, without insufflation, by forcing the trocar 650 and the cannula 624 down the shaft of the pneumo-needle 610 prior to creating pneumo-peritoneum, a technique that results in superior results.

Prior to the present invention, only very experienced surgeons would make a direct insertion of the trocar without insufflation. The present invention gives surgeons more confidence that the direct insertion step can be made with a minimum of risk to the patient. That would encourage more surgeons to use the direct trocar insertion technique which has advantages to the patient.

After the initial pilot hole has been formed by the pneumo-needle 610 and the surgeon has released his or her grasp of the abdomen 80, the surgeon then grasps the reducer housing 618 and employs the pusher features 636 to push the reducer housing 618 forward until it comes into contact with cannula stop 616. Because the trocar cutting tip 628 is concentrically located with respect to the shaft of pneumo-needle 610, then the trocar 650 and the cannula 624 pass down the shaft of the pneumo-needle 610 to the exact depth and location desired.

After the trocar 65 and cannula 624 have reached full depth as established by cannula stop 616, the surgeon then attaches an insufflation hose to stop cock 608 and the abdominal cavity 84 is inflated. When completed, the insufflation hose is removed from stop cock 608 and is then attached to cannula stop cock 622 which is then rotated to the open position so that cavity pressure can be maintained.

Needle retainer 612 can be removed in the following manner. The pneumo-needle sub-assembly 100 and 200, as illustrated in FIGS. 4A, 4B and 7C, is removed first by depressing the needle retainer latch 614, thereby unlocking graduator 646 on needle shaft 610 and permitting the sub-assembly to be separated freely from the needle retainer 612 and trocar 650. Trocar seal 24, as illustrated in FIG. 3, prevents gas leakage. Reducer housing lock 620 is then activated with one hand. The surgeon, using the other hand, rotates the needle retainer 612 until it clears the cannula tube 624. The distal face 638 of the needle retainer 612 includes a slot that allows the cannula 624 to easily slip out. Needle retainer 612 can then be separated from the reducer housing 618 since they are held together by a snap fit. Should the surgeon desire to utilize a stabilizer 39 and an abdominal lock 41, reducer housing 618 must be replaced with reducer housing 36 so that the stabilizer 39 can be attached. In either case, the surgeon is now ready to perform standard well known procedures.

While the invention has been described with reference to the preferred embodiment thereof, it will be appreciated by those of ordinary skill in the art that various modifications can be made to the structure and function of the invention without departing from the spirit and scope of the invention as a whole.

I claim:

1. A surgical apparatus for use by a surgeon for introducing a cannula into a patient, said apparatus comprising:
   a pneumo-needle having a shaft with a long axis and a first and a second end, a cutting tip located at said first end of said shaft, and a central channel running through said shaft;
   a knob means located at said second end of said pneumo-needle shaft;
   a trocar having a tip, a central channel and a long axis running through said central channel, such that said pneumo-needle is locatable within said central channel;
   a cannula surrounding said trocar, said cannula having a lumen therethrough;
   a reducer housing attached to said cannula and at least partially surrounding said pneumo-needle;
   a needle retainer means selectively attachable to said pneumo-needle for limiting the depth of penetration of said needle into said patient;
   a pneumo-needle retainer latch connected to said needle retainer means for selectively locking said pneumo-needle with respect to said needle retainer means; and,
   a locking means attached to said needle retainer means for selectively locking said reducer housing with respect to said needle retainer means.

2. The apparatus of claim further comprising:
   a cannula stop means attached to said needle retainer means for limiting the depth of penetration of said trocar and said cannula into said patient.

3. The apparatus of claim 2 wherein said reducer housing includes pusher means for manipulation by said surgeon.

4. The apparatus of claim 3 further comprising:
   first graduation means located on said needle retainer means for adjusting the location of said cannula stop means with respect to said needle retainer means.

5. The apparatus of claim 4 further comprising:
   second graduation means located on said pneumo-needle for adjusting the location of said pneumo-needle with respect to said needle retainer means.

6. The apparatus of claim 5 further comprising:
   a cannula housing attachable to said cannula; and,
   a duck bill seal means located within said cannula housing for sealing said cannula lumen,
   wherein said duck bill seal means located within said cannula housing prevents leakage of insufflation gas from said patient when said cannula is introduced into said patient.

7. The apparatus of claim 6 further comprising:
   an obturator means located within said central channel of said pneumo-needle.

8. The apparatus of claim 7 further comprising:
   a single cycle lock means for locking said obturator means with respect to said cutting tip of said pneumo-needle.

9. The apparatus of claim 8 wherein said knob means includes an obturator spring means for normally biasing said obturator out of the cutting tip of said pneumo-needle; and,
   an obturator release button for releasing said obturator means and said obturator spring means, thereby permitting said obturator means to be selectively biased inward from the cutting tip of said pneumo-needle.

10. The apparatus of claim 9 wherein said pneumo-needle emerges eccentrically from said tip of said trocar and said long axis of said pneumo-needle is offset a distance D from said long axis of said trocar.

11. The apparatus of claim 10 wherein said tip of said trocar comprises a stamped tip.

12. The apparatus of claim 11 further comprising:
   stabilizer means attached to said reducer housing for setting and gauging the depth of penetration of said cannula.

13. The apparatus of claim 12 further comprising:

seal means located within said reducer housing and attached to said reducer housing for sealing the interior of said reducer housing with respect to said cannula.

14. The apparatus of claim 13 wherein said stabilizer means includes a stabilizer lock, wherein said stabilizer lock engages the interior of a wound to prevent the premature withdrawal of said cannula from said wound.

15. The apparatus of claim 14 wherein said stamped tip of said trocar is formed from a flat blank of stainless steel, cut to form at least three upstanding edges, and rolled so as to form said trocar tip.

16. The apparatus of claim 15 wherein said trocar tip has a point and further wherein said pneumo-needle is offset so that one edge of said cutting tip of said pneumo-needle is substantially tangent to the point on the tip of said trocar.

17. The apparatus of claim 16 further comprising:

a stabilizer latch means attached to said stabilizer means for selectively immobilizing said reducer housing with respect to said stabilizer means.

18. The apparatus of claim 17 further comprising:

pneumo-needle duck bill seal means attached to said graduator means for sealing the lumen of said pneumo-needle, wherein said pneumo-needle seal means prevents the escape of insufflation gas from the abdominal cavity through the lumen of said pneumo-needle.

19. The apparatus of claim 18 further comprising:

trocar duck bill seal means located within said trocar for sealing the lumen of said trocar, wherein said trocar duck bill seal means seals said trocar lumen to prevent the escape of insufflation gas from the abdominal cavity through said trocar lumen.

20. The apparatus of claim 19 further comprising:

shuttle means attached to said trocar for covering the tip of said trocar when said trocar is withdrawn from said cannula.

21. A method for use by a surgeon for introducing a cannula into a patient through the use of a surgical apparatus including a pneumo-needle having a shaft and a sharp cutting tip, a trocar including a cutting tip surrounding said pneumo-needle, a cannula surrounding said trocar and said pneumo-needle, a knob attached to one end of said pneumo-needle, a needle retainer selectively lockable to said pneumo-needle, and a reducer housing attached to said cannula and lockable with respect to said needle retainer, said method comprising the steps of:

pushing said pneumo-needle into said patient to a predetermined depth; and, pushing said trocar and cannula simultaneously down the shaft of said pneumo-needle substantially to said predetermined depth.

22. A surgical apparatus for use by a surgeon for introducing a cannula into a patient, said apparatus comprising:

a pneumo-needle having a shaft with a long axis and a first and a second end, a cutting tip located at said first end of said shaft, and a central channel running through said shaft;

a knob means located at said second end of said pneumo-needle shaft;

a trocar having a tip, a central channel and a long axis running through said central channel, such that said pneumo-needle is locatable within said central channel;

a needle retainer means selectively attachable to said pneumo-needle for limiting the depth of penetration of said pneumo-needle into said patient, said needle retainer means including a front face; and, a pneumo-needle retainer latch connected to said needle retainer means for selectively locking said pneumo-needle with respect to said needle retainer means, wherein said front face of said needle retainer means limits the depth of penetration of said pneumo-needle into said patient.

23. A surgical apparatus for use by a surgeon for introducing a cannula into a patient, said apparatus comprising:

a pneumo-needle having a shaft with a long axis and a first and a second end, a cutting tip located at said first end of such shaft, and a central channel running through said shaft;

a knob means located at said second end of said pneumo-needle shaft;

a trocar having a tip, a central channel and a long axis running through such central channel, such that said pneumo-needle is locatable within said central channel;

a needle retainer means selectively attachable to said pneumo-needle for limiting the depth of penetration of said pneumo-needle into said patient; and, a cannula stop means supported by said needle-retainer means for limiting the depth of penetration of said trocar and said cannula into said patient, wherein said needle retainer means limits the depth of penetration of said pneumo-needle into said patient after which said cannula stop means limits the depth of penetration of said trocar and said cannula as they pass over said pneumo-needle into said patient.

* * * * *